(12) United States Patent
Gagnon

(10) Patent No.: US 9,809,639 B2
(45) Date of Patent: Nov. 7, 2017

(54) PURIFICATION OF BIOLOGICAL PRODUCTS BY CONSTRAINED COHYDRATION CHROMATOGRAPHY

(75) Inventor: Peter Stanley Gagnon, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 248 days.

(21) Appl. No.: 14/124,706

(22) PCT Filed: Jun. 1, 2012

(86) PCT No.: PCT/SG2012/000199
§ 371 (c)(1),
(2), (4) Date: Apr. 28, 2014

(87) PCT Pub. No.: WO2012/169970
PCT Pub. Date: Dec. 13, 2012

(65) Prior Publication Data
US 2014/0227766 A1    Aug. 14, 2014

Related U.S. Application Data

(60) Provisional application No. 61/494,669, filed on Jun. 8, 2011, provisional application No. 61/494,687, filed (Continued)

(30) Foreign Application Priority Data

Nov. 14, 2011 (SG) .................. 201108397

(51) Int. Cl.
*G01N 33/53* (2006.01)
*C12Q 1/70* (2006.01)
(Continued)

(52) U.S. Cl.
CPC ............. *C07K 14/75* (2013.01); *B01D 15/08* (2013.01); *B01D 15/166* (2013.01); *C07K 1/16* (2013.01);
(Continued)

(58) Field of Classification Search
None
See application file for complete search history.

(56) References Cited

U.S. PATENT DOCUMENTS

| | | |
|---|---|---|
| 2003/0155300 A1 | 8/2003 | Afeyan et al. |
| 2004/0106184 A1* | 6/2004 | Senesac ............. C12N 7/00 435/239 |

(Continued)

FOREIGN PATENT DOCUMENTS

| | | |
|---|---|---|
| CN | 1680550 | 10/2005 |

OTHER PUBLICATIONS

Podgornik et al., "Convective Interaction Media (CIM)—Short later monolithic chromatographic stationary phases," Biotechnology Annual Review vol. 11: 281-333 (2005).*
(Continued)

*Primary Examiner* — Janet L Andres
*Assistant Examiner* — M. Franco Salvoza
(74) *Attorney, Agent, or Firm* — Pillsbury Winthrop Shaw Pittman LLP

(57) ABSTRACT

Materials and methods for use of constrained cohydration agents in the purification of biological materials such as antibodies, viruses, cells, and cellular organelles in connection with convective chromatography, fluidized bed or coprecipitation applications.

36 Claims, 7 Drawing Sheets

Related U.S. Application Data on Jun. 8, 2011, provisional application No. 61/653,950, filed on May 31, 2012.

(51) Int. Cl.
| | | |
|---|---|---|
| C12Q 1/02 | (2006.01) | |
| C12M 1/00 | (2006.01) | |
| C07K 14/75 | (2006.01) | |
| B01D 15/16 | (2006.01) | |
| C07K 1/16 | (2006.01) | |
| C07K 16/06 | (2006.01) | |
| B01D 15/08 | (2006.01) | |
| C07K 14/755 | (2006.01) | |
| C12N 7/00 | (2006.01) | |
| B01D 15/18 | (2006.01) | |
| B01D 15/38 | (2006.01) | |

(52) U.S. Cl.
CPC .......... *C07K 14/755* (2013.01); *C07K 16/065* (2013.01); *C12N 7/00* (2013.01); *B01D 15/1807* (2013.01); *B01D 15/3885* (2013.01); *C12N 2795/00* (2013.01)

(56) References Cited

U.S. PATENT DOCUMENTS

| | | | | |
|---|---|---|---|---|
| 2005/0136477 A1* | 6/2005 | Akhavan-Tafti | ....... | C07H 21/02 435/6.12 |
| 2007/0000838 A1* | 1/2007 | Shih | ..................... | G01N 30/466 210/656 |
| 2007/0125711 A1* | 6/2007 | Bergstrom | ............. | B01J 20/286 210/656 |
| 2007/0213513 A1* | 9/2007 | Van Alstine | ....... | B01D 15/1864 530/416 |
| 2009/0247735 A1* | 10/2009 | Gagnon | ................. | C07K 1/165 530/413 |
| 2010/0135987 A1* | 6/2010 | Hickman et al. | .......... | 424/130.1 |

OTHER PUBLICATIONS

Fujito et al., "Elution of Viruses by Ionic and Nonionic Surfactants," Applied and Environmental Microbiology, vol. 62, No. 9:3470-3473 (1996).*
Jungbauer et al., "Polymethycrylate monoliths for preparative and industrial separation of biomolecular assemblies," Journal of Chromatography A 1184: 62-79 (2008).*
Strauss et al., "Understanding the Mechanism of Virus Removal by Q Sepharose Fast Flow Chromatography During the Purification of CHO-Cell Derived Biotherapeutics," Biotechnology and Bioengineering, vol. 104, Issue 2: 371-380 (2009).*
Burden et al., "A monolith purification process for virus-like particles from yeast homogenate," Journal of Chromatography 8, 880: 82-89 (2012).*
Arakawa et al. "Mechanism of Protein Salting In and Salting Out by Divalent Cation Salts: Balance between Hydration and Salt Binding," Biochemistry 23: 5912-5923 (1984).*
International Search Report dated Sep. 21, 2012 in International Patent Application No. PCT/SG2012/000199 (4 Pages).
Sun, Xinghua et al, "Study of hydrophobic interaction based binding of immunoglobulin G on synthetic membranes", Journal of Membrane Science, vol. 344, Nov. 15, 2009, pp. 165-171.
Gagnon, Pete, "Technology trends in antibody purification", Journal of Chromatography A, vol. 1221, Jan. 2012, pp. 57-70.
Kumar B. Prem et al.,"Production of Human Anti-Glycophorin-A Monoclonal Antibodies and Their Purification by Pseudoaffinity Chromatography Using a Convective Interaction Media Monolithic Column", Hybridoma, vol. 31, Apr. 17, 2012, pp. 105-110.
Arakawa, Tsutomu et al., "Preferential interactions of proteins with salts in concentrated solutions", Biochemistry, vol. 21, Dec. 1982, pp. 6545-6552.
Arakawa, Tsutomu, "The mechanism of increased elution volume of proteins by polyethylene glycol", Analytical Biochemistry, vol. 144, Jan. 1985, pp. 267-268.
Arakawa, Tsutomu et al., "Preferential interactions of proteins with solvent components in aqueous amino acid solutions", Archives of Biochemistry and Biophysics, vol. 224, Jul. 1, 1983, pp. 169-177.
Arakawa, Tsutomu et al., "Mechanism of poly(ethylene glycol) interaction with proteins", Biochemistry, vol. 24, Nov. 19, 1985, pp. 6756-6762.
Bhat, Rajiv et al., "Steric exclusion is the principal source of preferential hydration of proteins in the presence of polyethylene glycols", Protein Science, vol. 1, Sep. 1992, pp. 1133-1143.
Von Der Haar, Friedrich, "Purification of proteins by fractional interfacial salting out on unsubstituted agarose gels" , Biochemical and Biophysical Research Communications , vol. 70, Jun. 7, 1976, pp. 1009-1013.
Jungbauer, Alois et al., "Chromatographic Media for Bioseparation", Journal of Chromatography A, vol. 1065, Feb. 11, 2005, pp. 3-12.
Gagnon, Pete et al., "Method for obtaining unique selectivities in ion-exchange chromatography by addition of organic polymers to the mobile phase", Journal of Chromatography A, vol. 743, Aug. 30, 1996, pp. 51-55.
Gagnon, Pete, "Improved antibody aggregate removal by hydroxyapatite chromatography in the presence of polyethylene glycol", Journal of Immunological Methods, vol. 336, May 5, 2008, pp. 222-228.
Lendero Krajnc, Nika et al., "Adsorption behavior of large plasmids on the anion-exchange methacrylate monolithic columns", Journal of Chromatography A, vol. 1218, pp. 2413-2424.
Levy, M. Susana et al., "Biochemical engineering approaches to the challenges of producing pure plasmid DNA", Trends in Biotechnology, vol. 18, Jul. 1, 2000, pp. 296-305.
Hahn, Rainer et al., "Mass transfer properties of monoliths", Separation Science and Technology, vol. 37, Feb. 15, 2007, pp. 1545-1565.
Strancar, Ales et al., "Short monolithic columns as stationary phases for biochromatography", Advances in Biochemical Engineering/Biotechnology, vol. 76, pp. 49-85.

* cited by examiner

Figure 4. Analytical SEC of IgG purified on CCC-nanoparticles. The left-hand frame illustrates the profile of unpurified cell supernatant. The right-hand frame illustrates the profile of IgG purified on CCC-nanoparticles. Aggr refers to aggregates. HCP refers to host cell protein. NP debris refers to nanoparticle debris.

PURIFICATION OF BIOLOGICAL PRODUCTS BY CONSTRAINED COHYDRATION CHROMATOGRAPHY

This application is a U.S. national phase entry of International Patent Application No. PCT/SG2012/000199, filed Jun. 1, 2012, entitled *Purification Of Biological Products By Constrained Cohydration Chromatography*, which claims priority to U.S. Provisional Patent Application 61/494,669, filed on Jun. 8, 2011, U.S. Provisional Patent Application 61/494,687, filed on Jun. 8, 2011, Singapore Patent Application No. 201108397-9, filed on Nov. 14, 2011 and U.S. Provisional Patent Application 61/653,950, filed on May 31, 2012, each of which are incorporated herein by reference in their entireties.

FIELD OF THE INVENTION

This invention relates to methods for enhancing purification of biological products. It relates particularly to methods for enhancing purification of virus and purification of antibodies.

BACKGROUND OF THE INVENTION

Chromatography methods typically rely on exploitation of a solid surface that bears at least one chemical functionality to actively engage in interactions with biomolecules in order to sort the components of a complex sample according to that chemical functionality. These methods are called adsorptive chromatography methods. Surface chemistries differ among adsorptive methods, along with the chemical means to release bound components, but the operational format is the same. One example is bioaffinity chromatography, in which an inert surface is substituted with a biological ligand specific for a component of interest from a complex sample. The component of interest binds, the rest do not, and the component of interest is subsequently released by changing the chemical conditions. Ion exchange chromatography is representative of a greater diversity of methods. An inert surface is substituted covalently with a charged chemical group. In the case of anion exchange chromatography, the chemical group is positively charged. Sample components of sufficient negative charge bind, with the most negatively charged binding most strongly. Sample components lacking sufficient negative charge fail to bind. Bound components can be released in order of the strength of their interaction by the application of an increasing gradient of salt, which imposes a gradually increasing degree of disruption to the charge interactions, releasing the bound components in order of the intensity of their interaction with the anon exchanger. Except for differences of chemistry, the same operational format is applied to cation exchange chromatography, hydrophobic interaction chromatography, reversed-phase chromatography, and numerous examples of so-called mixed-mode chromatography, including hydroxyapatite.

An exception to the adsorptive methods reliance upon chemical functionality is size exclusion chromatography (SEC), also known as gel filtration and gel permeation chromatography. Chemical interactions between molecules and the surface of the media in such applications are effectively nil. SEC works by the differential diffusion of sample components into the pores of particles packed in a column. Very large components are excluded from the pores and pass only through the interparticle space. (Arbitrarily) mid-sized molecules diffuse into the larger pores. This gives them access to a larger fluid volume that the excluded molecules that have access to only the interparticle space. (Arbitrarily) small molecules may diffuse into all of the pores, which gives them access to a yet greater fluid volume. The greater the fluid volume with which a given size class of molecules is in equilibrium, the larger the volume of fluid required to displace them from the column. Thus large molecules elute first from SEC columns, followed in order by molecules of decreasing size.

Precipitation methods are well-known throughout the field of biology, including for purification of proteins and viruses. Two of the most common methods, so-called salt precipitation and PEG precipitation, exploit a force known as preferential exclusion. The term began to be used widely in the early 1980s and has since become the accepted terminology for describing the interactions of dissolved molecules (solutes) with proteins [1-5]. Preferentially excluded solutes interact with proteins in such a way that it leaves the proteins surrounded by a layer of water that is deficient in the preferentially excluded solute. This solute-deficient zone is referred to as the zone of preferential hydration, or preferential hydration shell, or sheath. When preferentially hydrated proteins encounter one another in solution, their preferential hydration sheaths merge. The higher the concentration of the excluded solute, the more strongly the two proteins remain associated. So-called kosmotropic salts, such as ammonium sulfate, sodium citrate, and potassium phosphate are strongly excluded from protein surfaces. Nonionic organic polymers such as polyethylene glycol (PEG) are also known to be strongly excluded from protein surfaces [3-5]. These precipitation methods are performed by dissolving large amounts of the preferentially excluded agent in a sample containing the species to be precipitated. As the preferentially excluded agent ascends toward a threshold level, it causes target species that randomly contact one another to remain associated by sharing the water from their respective preferential hydration sheaths. This leads to formation of large insoluble aggregations that eventually precipitate, after which they can be recovered by centrifugation or filtration. Precipitation methods however impose undesirable limitations, chief of which is that purification performance is recognized as universally inferior to chromatography methods, and also suffers from a high degree of variability from batch to batch, especially in conjunction with variations in the concentration of the product to be precipitated. Recovery is likewise variable, and can be prohibitively low when the product of interest is present at low concentrations. These issues are known to derive from the dependency of precipitation methods on the interactions of highly heterogeneous surfaces, namely the proteins being precipitated. Commercial applications persist, but most have been replaced by chromatography because the latter usually offers better recovery and a higher degree of purity. Interest in precipitation methods remains however because they potentially offer higher productivity than chromatography, the materials are cheaper, and the equipment is simpler to operate.

The force of preferential exclusion has been used to enhance existing interactions between proteins and the surfaces of adsorptive chromatography media. Salts are well known to enhance binding in hydrophobic interaction chromatography (HIC). This is the standard way in which binding is achieved with this technique. They have also been used to enhance binding with some affinity methods, such as protein A affinity chromatography (6). Ammonium sulfate was reported to cause binding of proteins to a non-functionalized porous particle chromatography support in the 1970s (7) but was not pursued, possibly due to limitations in the method of sample preparation and application to the column. Direct addition of excess ammonium sulfate to a sample creates precipitates that clog chromatography columns. Addition of non-precipitating amounts of salt would be expected to support low capacities, as apparently experienced in reference 7.

The force of preferential exclusion has also been used to enhance binding of adsorptive chromatography methods with nonionic polymers such as PEG. In contrast to salts, it does not work with HIC because the inherent hydrophobicity of the PEG interferes directly with the binding mechanism. PEG can be used to precipitate proteins inside a HIC column, and the proteins can be subsequently resolubilized, but this is not adsorptive chromatography and it lacks utility: capacity and resolution are prohibitively limited [6]. PEG has been used to enhance binding with affinity chromatography [6], ion exchange chromatography [8], and hydroxyapatite chromatography [9], and it is known to interfere with the separation achieved in SEC [10]. In all these cases it retards elution, especially of large molecules such as aggregates, which sometimes aids in their separation [9], but its use is discouraged by its high viscosity. High viscosity is a particular problem for all methods of chromatography on porous particles because they depend on diffusion to transport proteins to, within, and from the pores. Diffusivity is directly proportional to viscosity, so column performance drops in direct proportion to the PEG concentration. Viscosity also increases shear forces that occur in the interparticle space of chromatography columns. These limitations are tolerated in some instances because PEG has been shown to more strongly affect the binding of large molecules in comparison to small one, thus enhancing the ability of hydroxyapatite to improve fractionation of antibody aggregates from nonaggregated antibody [7,8]. Since both liabilities increase in direct proportion to PEG concentration, it is not surprising that its broader application has been avoided.

Fluidized particle beds provide an alternative to chromatography in packed beds. In fluidized beds, particles are dispersed throughout the sample containing the target molecule. After binding the target molecule, the particles are concentrated, so that unbound contaminants can be washed away, and so that the bound product can be eluted at a high concentration. Concentration of the particles can be achieved by various methods. Particles with density greater than water can be sedimented. Iron-core particles can be concentrated in a magnetic field. Particles may also be concentrated on filtration membranes. Particle size may vary from less than 100 nm to more than 100 microns. The surface of particles for expanded bed chromatography is normally functionalized with chemical groups that interact strongly with the intended target molecule. For example, many publications report the immobilization of protein A on fluidized particles to capture and purify IgG. Other publications describe functionalization with charged groups, hydrophobic groups, metal affinity groups, and groups employing multiple chemistries. These various functionalizations allow fluidized bed formats to offer the same range of chemical selectivities offered by same the functionalizations in fixed bed chromatography methods.

The importance of fluidized beds is that they offer the physical handling characteristics to overcome one of the most serious limitations of packed beds: low productivity. Traditional porous particle columns require slow flow rates that impose excessive overall process time intervals. These time intervals are multiplied when the chromatography media are so expensive as to force users to run multiple cycles on a reduced volume column because the price of sufficient chromatography material to run a process in a single cycle is prohibitive. However, for any method to fulfill the needs of initial product capture from crude biological samples, also requires that it be able to achieve good binding capacity under near physiological pH and salt concentration. Every known chromatography method has been evaluated for this application, but only bioaffinity chromatography has fulfilled this requirement to date. All others require substantial modification of conditions and/or are rendered ineffective by components of cell culture supernatants.

REFERENCES (1) Arakawa, T. and Timasheff, S. N. (1982). Preferential interactions of proteins with salts in concentrated solutions. *Biochemistry* 21, 6545-6552
(2) Arakawa, T. and Timasheff, S. N. (1984). Mechanism of protein salting in and salting out by divalent cation salts: balance between hydration and salt binding. *Biochemistry* 23, 5912-5923.
(3) Arakawa, T. and Timasheff, S. N. (1983). Preferential interactions of proteins with solvent components in aqueous amino acid solutions. *Arch. Biochem. Biophys.* 224, 169-177.
(4) Arakawa, T. and Timasheff, S. N. (1985). Mechanism of poly(ethylene glycol) interaction with proteins. *Biochemistry* 24, 6756-6762.
(5) Bhat, R., Timasheff, S., Steric exclusion is the principal source of preferential hydration of proteins in the presence of polyethylene glycols. *Prot. Sci.*, 1, 113-1143 (1992).
(6) P. Gagnon, (1996) Purification Tools for Monoclonal Antibodies, Validated Biosystems, Tucson.
(7) von der Haar, F., (1976) Purification of proteins by fractional interfacial salting out on unsubstituted agarose gels. *Biochem. Biophys. Res. Comm.*, 70 (3) 1009-1013.
(8) P. Gagnon, B. Godfrey, D. Ladd, (1996) Method for obtaining unique selectivities in ion-exchange chromatography by addition of organic polymers to the mobile phase, *J. Chromatogr. A* 743 51-55
(9) P. Gagnon (2008) Improved antibody aggregate removal by hydroxyapatite chromatography in the presence of polyethylene glycol, *J. Immunol. Met.* 336 222-228
(10) T. Arakawa (1985) The mechanism of increased elution volume of proteins by polyethylene glycol, *Analyt. Biochem.*, 144 267-268.

SUMMARY OF THE INVENTION

Methods and compositions and kits adapted for performing the invention are provided. In certain embodiments, the invention provides a method for purification of a target species of biological origin in a sample including the steps of (i) contacting the sample with the hydrated surface of an undissolved material and (ii) contacting the sample and undissolved material with a preferentially excluded agent in an amount sufficient to cause at least a fraction of the now preferentially hydrated target species to be retained at the now preferentially hydrated surface of the undissolved material. This form of association is herein also referred to as constrained cohydration; the preferentially excluded agent is sometimes referred to as the constraining agent; and for brevity, preferentially hydrated molecules and surfaces are referred to simply as "hydrated." In certain such embodiments, more than 50% of the hydrated target species is retained at the hydrated surface of the undissolved material by the constraining agent and in some embodiments substantially all of the target species is retained. In certain such embodiments, at least one individual of the hydrated target species is retained at the hydrated surface exclusively by constrained co-hydration caused by the presence of the constraining agent. In certain such embodiments under such conditions substantially all of the target species is retained at the hydrated surface exclusively by constrained co-hydration caused by the presence of the constraining agent. In certain such embodiments, the exclusive retention of the hydrated target species at the hydrated surface by constrained co-hydration due to the presence of the constraining agent can be demonstrated by termination of such retention through the removal or reduction of the concentration of the constraining agent.

In certain embodiments of the invention, methods and associated compositions and kits are provided for practice of the invention in the context of a tripartite system separation, precipitation method, fluidized bed process or a convective chromatographic process.

DETAILED DESCRIPTION OF THE INVENTION

Figure 1:
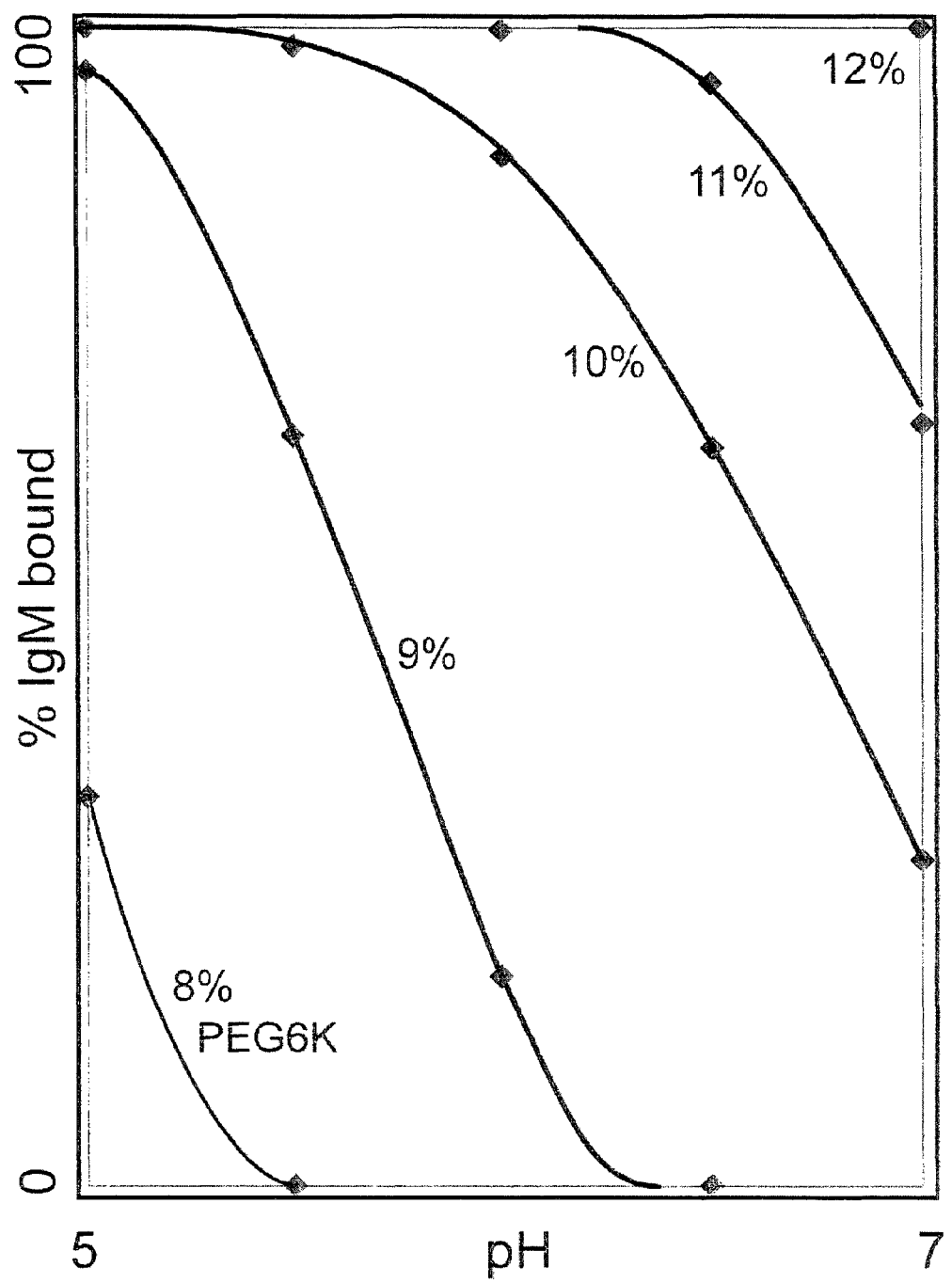
FIG. 1 shows the relationship between the percentage of IgM retained by constrained co-hydration at the surface of a hydrated monolith and pH for different percentages of the preferentially excluded agent, PEG-6000 (8%, 9%, 10%, 11%, and 12%) as described in Example 5.

Methods and compositions and kits adapted for performing the invention are provided. In certain embodiments, the invention provides a method for purification of a target species of biological origin in a sample including the steps of (i) contacting the sample with a hydrated surface of an undissolved material and (ii) contacting the sample and undissolved material with a preferentially excluded agent in an amount sufficient to cause at least a fraction of the now preferentially hydrated target species to be retained at the now preferentially hydrated surface of the undissolved material. In certain such embodiments, more than 50% of the hydrated target species is retained at the hydrated surface of the undissolved material by the constraining agent and in some embodiments substantially all of the target species is retained. In certain such embodiments, at least one individual of the hydrated target species is retained at the hydrated surface exclusively by constrained co-hydration caused by the presence of the constraining agent. In certain such embodiments under such conditions substantially all of the target species is retained at the hydrated surface exclusively by constrained co-hydration caused by the presence of the constraining agent. In certain such embodiments, the exclusive retention of the hydrated target species at the hydrated surface by constrained co-hydration due to the presence of the constraining agent can be demonstrated by termination of such retention through the removal or reduction of the concentration of the constraining agent.

In certain embodiments, the target species is a protein, antibody, clotting factor, cellular organelle, virus, virus-like particle, gene therapy vector or cell. In certain such embodiments, the sample is a cell culture harvest, a cell culture supernatant, a protein-containing solution derived from a cell culture, an antibody-containing solution derived from a cell culture, a virus-containing solution derived from cell culture, or a target species-containing solution from a previous stage of purification. In certain such embodiments, the target species is a protein. In others, the target species is a polyclonal or monoclonal antibody of the class IgA, IgD, IgE, IgG, or IgM or a fragment thereof. In others, the target species is a prokaryotic cell, eukaryotic cell, stem cell. In yet others, the target species is a virus, lipid enveloped virus, protein capsid virus or virus like particle. In others, the target species is an exosome, liposome, mitochondrion, chloroplast, lysosome, or other cellular organelle. In further embodiments, the target species is a clotting factor. As implied by target species named above, the invention offers particular utility for purification of target species that are large in nature.

In certain embodiments, the surface of the undissolved material has one or more polar chemical moieties. The polar chemical moiety may be in certain embodiments hydroxyl, polyhydroxyl, amine, imine, ureide, carbohydrate, amino acid, peptide, a cationic charged group or an anionic charged group. In certain such embodiments, the polar chemical moiety is a carbohydrate selected from the group consisting of glucose, mannose, galactose, lactose, a monosaccharide, a disaccharide and a polysaccharide. In others, the polar chemical moiety is a ureide selected from the group consisting of urea, uric acid, allantoin, hydantoin. In yet others, the polar chemical moiety is histidine, glycine, alanine, valine, leucine, isoleucine, methionine, phenylalanine, tryptophan, proline, serine, threonine, cysteine, tyrosine, asparagine, glutamine, lysine, arginine, or selenocysteine. In certain embodiments the surface may comprise combinations of such groups.

In certain embodiments, the constraining agent is one or more of a salt, a polysaccharide, a non-ionic organic polymer, an inorganic polymer, a kosmotropic salt, an ampholytic polymer having a multiple positive and negative charges, or an amino acid. In certain such embodiments, the constraining agent is ammonium sulfate, sodium citrate, potassium citrate, potassium phosphate, and sodium chloride. In certain such embodiments, the constraining agent is an aqueous soluble uncharged linear or branched non-ionic organic polymer. The constraining agent may be polyethylene glycol, polypropylene glycol, polyvinylpyrrolidone, dextran, starch, cellulose. In certain cases, the constraining agent is polyethylene glycol and PEG may have an average polymer weight between 100 and 10,000 D. In certain such embodiments, the average polymer weight for the PEG is between 600 and 8,000 D or is approximately any of 200, 300, 400, 600, 1,000, 1500, 1540, 4000, 6,000, or 20,000. In certain such embodiments, the polyethylene glycol is provided at a concentration between approximately 5% and approximately 25% (w/v). In certain such embodiments, the concentration of PEG is 5%, 6%, 7%, 8%, 9%, 10%, 11%, 12%, 13%, 14%, or 15% or a range between two of these values.

In certain embodiments, the undissolved material is a collection of organic nucleation centers. In certain embodiments, the organic nucleation centers consist of naturally occurring non-toxic organic compounds at supersaturating concentrations, the insoluble residue of which takes the form of nano- and/or microparticles particles with hydrated surfaces. In certain such embodiments, the organic nucleation centers may comprise a carbohydrate, ureide or peptide, or more complex composition. In certain such embodiments, an organic nucleation center with a hydrated surface in the presence of a constraining agent may retain one or more layers of the target species. In certain embodiments, the surface of the organic nucleation center may contain reactive elements that bind a monolayer of the target species, which in the presence of a constraining agent becomes the hydrated surface, on top of which multiple additional layers of the target species are retained by constrained cohydration. A particular advantage of performing the invention with naturally occurring organic nucleation centers is that they are relatively inexpensive compared to synthetic particles and they are generally biodegradable, thereby reducing processing expenses and environmental impacts.

In certain embodiments, the sample is contacted with the organic nucleation center prior to the step of contacting the sample with the constraining agent. In certain such embodiments, the method includes the additional steps of separating the supernatant containing contaminants from the organic nucleation centers having the target species retained at their surface.

In certain embodiments, the invention provides the additional step of dissociating the target species from the organic nucleation center by exposing the organic nucleation centers to conditions that promote the dissociation of the target species from the organic nucleation center and recovery of the re-solubilized target species from the organic nucleation centers. In certain such embodiments, the target species is dissociated from the organic nucleation center by substantially reducing the concentration of the constraining agent. In certain such embodiments, the salt concentration is increased sufficiently to reduce the effectiveness of the constraining agent to retain the target species at the hydrated surface of the organic nucleation center. In certain such embodiments, the sugar concentration is increased sufficiently to reduce the effectiveness of the constraining agent to retain the target species at the hydrated surface of the organic nucleation centers. In certain embodiments, the process includes one or more additional steps of washing the organic nucleation centers prior to dissociating the target species from the organic nucleation centers. In certain such embodiments, the washing solutions contain adequate concentration of one or more constraining agents to maintain retention of the target species at the hydrated surface of the organic nucleation centers. In certain such embodiments, the solutions used in the steps of dissociating the target species from the organic nucleation centers are substantially the same as the solutions used for the recovery of the target species.

In certain embodiments, the invention provides a kit including organic nucleation centers, and constraining agents configured for the convenient practice of a method of the invention.

In certain embodiments, the undissolved material comprises synthetic particles. In certain embodiments, such particles are nanoparticles or microparticles. In certain embodiments, the particles are magnetic, paramagnetic or of high-density. In certain embodiments, the particles are either metal-core particles having a polymer coating, metal core particles having a cellulose coating, glass particles, polyacrylate, polymethacrylate, styrenedivinylbenzene, thiophilic magnetic particles, cellulose coated tungsten carbide particles, silica particles, agarose particles, cellulose particles, or composite particles. In certain embodiments, the particle size is between about 100 nm and about 500 µm; or between about 10 nm and 500 nm; or between about 100 nm and about 50 µm; or between about 100 nm and about 4 µm; or between about 100 nm and about 3 µm; or between about 100 nm and about 1 µm; or between about 200 nm and about 2 µm; or between about 200 nm and about 500 nm; or between about 500 nm and about 1 µm; or between about 5 µm and about 50 µm.

In certain embodiments, the step of contacting the target sample with the particles occurs prior to the step of retaining the target species with the constraining agent. In certain embodiments, the method includes the additional steps of (i) separating the particles with the target species associated with the hydrated surface of the particles from the liquid phase and (ii) dissociating the target species from the particles. In certain such embodiments, the step of dissociating the target species comprises washing the particles with a solution where the solution either (i) does not contain the constraining agent, (ii) contains the constraining agent in an amount insufficient to retain the target species at the hydrated surface of the particles, (iii) contains an agent which effects dissociation of the target species from the hydrated surface of the particles, (iv) a combination of (i) and (iii), or (iv) a combination of (ii) and (iii).

In certain embodiments, if the surface of the particles includes many or strongly reactive chemical moieties, the pH, salt concentration, and other components of the buffers delivered to the column are selected to suspend direct interaction between the target species and such chemically reactive moieties during at least one step of the process, leaving the target species retained during that step exclusively by constrained cohydration mediated through the action of a constraining agent. In certain such embodiments, the agent which suspends interaction of the target species with chemically reactive moieties on the particle surface is selected from the group consisting of a chelating agent, a surfactant, a salt, a chaotrope, a change in pH, or a combination of agents and conditions. In certain such embodiments, the step of dissociating the target species from the particles may also include a chelating agent, a surfactant, a salt, a chaotrope, a change in pH, or a combination of agents and conditions to improve the recovery of the target species from the particles.

In certain embodiments, if the surface of the particles includes few or weakly reactive chemical moieties, the pH, salt concentration, and other components of the buffers delivered to the column may be selected to diminish or suspend direct interaction between the target species and such chemically reactive moieties, particularly during the dissociation step, in order to increase the recovery of the target species. In certain such embodiments, the agent which diminishes or suspends interaction of the target species with chemically reactive moieties on the particle surface is selected from the group consisting of a chelating agent, a surfactant, a salt, a chaotrope, a change in pH, or a combination of agents and conditions.

In certain embodiments, the constraining agent is added to the sample and the particles over a period of time from about one minute to about five hours; between 2 min and 15 min; between 2 min and 30 min; between 10 min and 30 min; between 2 min and 2 hours; or between about 2 min and 1 hour. In certain embodiments, the particles are separated from the liquid component of the mixture by centrifugation, sedimentation, decantation, subjecting the mixture to a magnetic field, or by filtration. In certain such embodiments, the separated particles are washed with a solution comprising the constraining agent.

In certain embodiments, the step of dissociating is carried out in a single step of adding a dissociating buffer to the particles. In other embodiments, the step of dissociating the target species is carried out incrementally through the reduction of the concentration of the constraining agent.

In certain embodiments, the method is performed prior to or after a method for fractionating the target species from other materials is performed and the method for fractionating is selected from the group consisting of high performance liquid chromatography, affinity chromatography, protein A chromatography, protein G chromatography, anion exchange chromatography, cation exchange chromatography, hydrophobic interaction chromatography, immobilized metal affinity chromatography, precipitation methods, polyethylene glycol precipitation, octanoic acid precipitation, centrifugation, and ultracentrifugation.

In certain embodiments, the undissolved material is a fixed-bed convective chromatography material. In certain such embodiments, the convective chromatography material is selected from the group consisting of a monolith, a membrane, and a column packed with nonporous particles. In certain such embodiments, the convective chromatography material is nonporous silica particles. In certain embodiments, the convective chromatography material is a monolith. In certain embodiments, the monolith may be made of polyacrylate, polymethacrylate, styrenedivinylbenzene or silica. In certain such embodiments, the monolith has average channel size between about 1 micron and 200 micron. In certain embodiments, the channel size is between about 1 micron and 2 microns; between about 10 micron and 20 microns; or between about 20 micron and 200 microns. In certain embodiments, the monolith is coated with a polymer. In certain embodiments, the monolith is chemically modified to increase the degree of surface hydration. In certain embodiments, the convective chromatography material surface is hydroxylated.

In certain embodiments, if the convective chromatography material surface includes charged moieties, the pH and salt concentration of the buffers delivered to the column are selected to suspend electrostatic binding of the target species to such charged moieties during at least one step of the process, during which the target species is retained exclusively by constrained cohydration.

In certain embodiments, the step of contacting the sample with the hydrated surface of the convective chromatography material is performed in the presence of a constraining agent. In certain such embodiments, the convective chromatography material is first equilibrated with a solution containing a concentration of constraining agent sufficient to retain the target species. In certain such embodiments, the sample may be applied in such a way that it is mixed with a concentrated solution of the constraining agent immediately before the mixture contacts the convective chromatography material in order to minimize or prevent precipitation of the sample components before they are contacted with the convective chromatography material. In certain such embodiments, this is achieved by loading sample through one pump, loading the concentrated constraining agent through another pump, plumbing the system so that they meet at a mixer immediately in advance of contacting the convective chromatography material, and proportioning the flow rates of the two pumps to deliver the concentration of constraining agent required to achieve retention of the target species on the hydrated surface of the convective chromatography material. This method of sample application is hereinafter referred to as in-line dilution. In certain such embodiments, the method provides the additional steps of washing the hydrated convective chromatography material with a solution containing an adequate concentration of preferentially excluded agent to maintain retention of the target species but rinse away unretained contaminants. In certain such embodiments, the convective chromatography material may be contacted with a solution to dissociate the target species from the convective chromatography material. In certain such embodiments, the step of dissociating the target species comprises washing the convective chromatography material with a solution where the solution either (i) does not contain the constraining agent, (ii) contains the constraining agent in an amount insufficient to retain the target species at the preferentially hydrated surface of the convective chromatography material, (iii) contains an agent which effects dissociation of the target species from the preferentially hydrated surface of the convective chromatography material, (iv) a combination of (i) and (iii), or (iv) a combination of (ii) and (iii).

In certain embodiments, the agent which effects dissociation of the target species from the hydrated surface of the convective chromatography material is selected from the group consisting of a surfactant, a chaotrope, a salt, a sugar, or an amino acid.

In certain embodiments, the method of the invention is performed prior to or after a method for fractionating the target species from other materials is performed and the method for fractionating is selected from the group consisting of high performance liquid chromatography, affinity chromatography, protein A chromatography, protein G chromatography, anion exchange chromatography, cation exchange chromatography, hydrophobic interaction chromatography, immobilized metal affinity chromatography, precipitation methods, polyethylene glycol precipitation, octanoic acid precipitation, centrifugation, and ultracentrifugation.

In certain embodiments, the undissolved material possesses chemically reactive moieties that can bind with the target species under a first set of conditions and not bind with the target species under a second set of conditions and wherein the method comprises a step of retaining the target species at the hydrated surface of the undissolved material by virtue of the additional presence of a preferentially excluded agent, under conditions otherwise identical to the second set of conditions above. In certain such embodiments, the step of retaining the target species at the hydrated surface of the undissolved material under the second set of conditions, the method comprises an additional step of washing the sample under the first set of conditions while the target species is bound to the undissolved material. In certain such embodiments, the first and second set of conditions are differentiated with respect to at least one of pH, conductivity and salt concentration.

In certain embodiments, the invention may be practiced with non-convective chromatography materials such as porous particles packed in chromatography columns. In certain such embodiments, the utility of the porous particle application may be extended or improved beyond what is possible with porous particles absent the invention, but as a general matter, the performance will be inferior to the invention as performed with convective chromatography media, or other forms of the invention.

In certain embodiments, the invention may be applied for so-called negative chromatography applications in which the target species is not retained by constrained cohydration while contaminants are retained and thus separated from the target species. In certain such embodiments with organic nucleation centers and synthetic particles, it is understood that the target species will remain in the supernatant while the contaminants to be removed will be retained by the particles. In certain such embodiments with fixed bed chromatography media, including either convective material or porous particle columns, it is understood that the target species will flow through the chromatography bed, while the contaminants to be removed will be retained. In addition to the term "negative chromatography" such applications are sometimes referred to as "flow-through methods."

It has been surprisingly discovered that the use of a 3-phase system created by dispersion of an excess of solid organic nucleation centers in biological preparations prior to addition of constraining agents results in shorter incubation times, better purity, better recovery, and better reproducibility than traditional 2-phase precipitation systems. Gradual addition of the constraining agent is a requirement of the method, whether it be a salt or non-ionic organic polymer. This suggests that the constraining agent causes the target species to form stable associations with the organic nucleation centers, instead of with each other. Since the hydrated chemical surface of the organic nucleation center is of a more uniform character than the highly heterogeneous surfaces of proteins and other precipitation target species, it follows that the partition coefficients should be better defined, leading to more refined fractionation, e.g., a higher degree of purity. Since the nucleation centers are provided in excess, it also follows that mass action should be more efficient and support higher recovery with shorter incubation times. The combination of uniformity and excess are consistent with better reproducibility, despite variations in the composition of the sample. Thus in certain embodiments the method overcomes the most undesirable limitations of traditional 2-phase precipitation systems. After co-precipitation of the target species with the organic nucleation centers, the supernatant may be removed by centrifugation or filtration. The target species may then be recovered from the organic nucleation center by exposing it to a solution lacking the constraining agent. The still-insoluble organic nucleation center may be subsequently removed by centrifugation or filtration.

It has been surprisingly discovered that in certain embodiments contacting a constraining agent with hydrated synthetic particles dispersed in a biological liquid promotes the selective binding of large proteins and other large biological products on the surface of the particles, and that the biological product can be subsequently recovered at unexpectedly high purity by reducing the concentration of the constraining agent. In certain embodiments, there is no requirement for strongly product-interactive chemical functionalities on the surface of the particles: neither affinity ligands, positive charges, negative charges, hydrophobic ligands, nor any combination thereof. Binding and elution can occur over a wide range of pH and conductivity conditions, making the method especially suitable for product capture from crude cell culture supernatants. In certain embodiments, the process entails dispersing particles in a biological sample containing a target species of interest, gradually adding a constraining agent to a concentration sufficient to create a stable association between the particles and the target species, then separating the particles from the contaminant bearing liquid. One or more washing steps can be applied by resuspending the particles in a clean buffer containing an adequate concentration of the constraining agent to keep the target species bound to the particles. This has the effect of diluting contaminant-bearing liquid that may have been entrapped in or between the particles. The product is finally dissociated from the particles by exposing them to a solution with a reduced concentration of the constraining agent. Experimental results demonstrate that the method of certain such embodiments supports product purity very similar to bioaffinity methods such as protein A affinity purification of IgG antibodies, and also overcomes the variable purity and recovery typical of precipitation methods. Experimental data further suggest that the reasons for the better performance derive from the overwhelming excess of a uniform hydrated surface to act as the preferred cohydration partner in the system. Perhaps the most surprising and remarkable feature of this approach is exemplified by starch-modified magnetic nanoparticles which support more than 90% purity and 90% recovery with a capacity 30 times higher than protein A affinity nanoparticles of the same architecture. These results suggest that particles are able to accumulate multiple layers of the chosen target species, in comparison with particles that rely solely on reactive surface chemical moieties which can accumulate only a monolayer of the target species.

It has also been surprisingly discovered that constraining agents, particularly including nonionic organic polymers, can be used in certain embodiments to achieve retention of biological products on the hydrated surface of convective chromatography media in the absence of a significant chemical attraction between the biological product and the surface. In certain embodiments, high capacity sample loading is achieved by loading sample though one pump line on a chromatograph, simultaneously loading a high concentration of a preferentially excluded agent through a second pump line, and mixing the two streams just prior to the convective chromatography support. This limits pre-column residence time of the mixture to such a short interval that precipitation does not occur to a sufficient degree to interfere with the process. Thus high capacity and high resolution can be achieved despite the high viscosity of the preferentially excluded solute, and they are maintained at flow rates more than 10 times higher than can be achieved with porous particle columns. This has the compound enabling effect of minimizing sample precipitation in advance of the chromatography support, since the pre-column residence time of the sample is inversely proportional to the flow rate. This enables the use of higher concentrations of the preferentially excluded agent, which favors higher binding capacity. After the target product is bound to the chromatography support, the bed can be washed with clean buffer to rinse away unbound contaminants. It is understood that in certain embodiments, the wash buffer will contain a sufficient concentration of a constraining agent to keep the product of interest bound to the surface. This step is followed by dissociation and recovery of the target product. This can be accomplished by reducing the concentration of the constraining agent that was used to achieve retention. Another valuable distinction of the method as practiced on monoliths and membranes is that high capacity and high resolution fractionation are maintained regardless of the size of the product being purified, so that the invention is as effective with virus particles as it is with proteins. Porous particle media give prohibitively inferior performance with large biological products. Another valuable distinction is that the invention is more gentle chemically than other methods thanks to the structure-stabilizing abilities of constraining agents, in combination with the lack of inter-particle shear within monoliths. Another valuable distinction is that practicing the invention with nonionic organic polymers suspends non-specific hydrophobic interactions that can lead to fouling of chromatography surfaces by small hydrophobic contaminants such as abound in cell culture supernatants. The remarkable overall result is that this unique combination of mechanism, method, and materials creates a system that works so well as to offer a highly competitive alternative to established adsorption chromatography methods, providing outstanding results where all other methods fail. Additionally the fractionation mechanism of certain embodiments of the invention is complementary to established methods and forms a valuable new addition to the tool set available to process developers and manufacturers.

Definitions And Terminology

Terms are defined and explained so that the invention may be understood more readily. Additional definitions are set forth throughout the detailed description.

"Amino acid" refers to a class of organic molecules of natural or synthetic origin that contain carbon, hydrogen, oxygen, and nitrogen in an arrangement including an amine group, a carboxylic acid, and a side chain. Examples suitable as organic nucleation centers favor species of low solubility. The effective concentration of such agents varies with the identity of the amino acid and the characteristics of the biological product being processed by the invention. By extension, small peptides may also be employed as organic nucleation centers. Examples of amino acids include but are not limited to glycine, which is soluble up to a concentration of about 2.5 M.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies, for example, can be classified into two categories: "Homoaggregates" refers to a stable association of two or more antibody molecules; "Heteroaggregates" refers to a stable association of one or more antibody molecules with one or more non-antibody molecules. The non-antibody component may consist of one or more entities from the group consisting of a nucleotide, an endotoxin, a metal ion, a protein, a lipid, or a cell culture media component.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function. "Antibody" may also include compound recombinant constructs, including so-called fusion proteins where the Fc portion an antibody is recombinantly fused to a non-antibody protein. "Antibody" may also include synthetic constructs, including so called enzyme conjugates where an enzyme or other protein is chemically coupled to an antibody.

"Carbohydrate" refers to a class of organic molecules of natural or synthetic origin that contain carbon, hydrogen, and oxygen with the general formula $C_m(H_2O)_n$. Species constituting organic nucleation centers suitable for performing certain embodiments of the invention include but are not limited to cellulose, starch, and poorly soluble sugars.

"Chromatography support" refers to a fixed chromatography bed that may be used to conduct chromatography. The chromatography support may comprise a monolith, a membrane, or a packed column of porous or non-porous particles.

"Constraining agent" (sometimes "preferentially excluded agent," "precipitating agent," preferentially excluded solute" or "constrained cohydration agent") as used in reference to certain embodiments of the invention, refers to an agent that causes the retention of biological target species on a hydrated surface by means of the mechanism herein referred to as constrained cohydration. In the broader literature some of such agents are commonly described as preferentially excluded solutes and precipitating agents. Preferentially excluded substances may include but are not limited to so-called kosmotropic salts, nonionic or zwitterionic organic polymers, some polysaccharides, and amino acids. One group of examples comprises but is not limited to so-called precipitating salts such as ammonium sulfate, sodium citrate, and potassium phosphate, among others. Another group comprises non-ionic organic polymers such polyethylene glycol (PEG), polypropylene glycol (PPG), and polyvinylpyrrolidone, among others. PEG has a structural formula $HO-(CH_2-CH_2-O)_n-H$. Examples include, but are not limited to compositions with an average polymer molecular weight ranging from less than 100 to more than 10,000 daltons, but more usually 3,000 to 8,000 daltons. Another group comprises amino acids such as glycine. Without being bound to any specific theory, it is believed that preferential exclusion refers to a condition in which the solvent immediately surrounding a protein for a distance of up to about 4 nm is deficient in the particular constraining agent. This zone is consequently said to be preferentially hydrated. When preferentially hydrated surfaces interact, they share some water, and give some water back to the bulk solvent. Since they are not able to regain that water while the constraining agent remains present, they are constrained to continue sharing their respective preferential hydration water. This condition is called constrained cohydration.

"Endotoxin" refers to a toxic heat-stable lipopolysaccharide substance present in the outer membrane of gram-negative bacteria that is released from the cell upon lysis.

"Exosomes" refers to a type of organelle associated with stem cells.

"Factor VIII" (factor eight) is clotting protein.

"Fibrinogen" is clotting protein.

"Hydrated surface" or "highly hydrated surface" or "hydrophilic surface" refers to surface that interacts strongly with water, potentially through hydrogen bonding, electrostriction, or some combination of the two mechanisms. Such interactions may be mediated by chemical groups such as hydroxyls, negative charges, or positive charges, or uncharged polar groups. The presence of hydratable chemical groups may be a basic feature of the native composition of a given material, such as a particle or convective chromatography material, or it may be added or enhanced by chemical modification to immobilize such groups on the surface, including but not limited to carbohydrates and ureides. So-called hydrophobic surfaces are generally considered not to be highly hydrated, but surfaces that include strongly hydratable groups in combination with hydrophobic residues may nevertheless be sufficiently hydrated to practice the invention.

"Kosmotropic salts" may include any of a variety of salts including but not limited to ammonium sulfate, sodium sulfate, potassium phosphate, sodium citrate, potassium citrate, and sodium chloride. The effective concentration of such salts varies with the identity of the salt and the characteristics of the biological product being processed by the invention.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the invention include but are not limited to dextran, starch, cellulose, polyethylene glycol (PEG), polypropylene glycol, and polyvinylpyrrolidone (PVP). PEG has a structural formula HO—(CH$_2$—CH$_2$—O)$_n$—H. Examples include, but are not limited to compositions with an average polymer molecular weight ranging from less than 100 to more than 10000 daltons. The average molecular weight of commercial PEG preparations is typically indicated by a hyphenated suffix. For example, PEG-6000 refers to a preparation with an average molecular weight of about 6,000 daltons. The effective concentration of such agents varies with the identity of the polymer and the characteristics of the biological product being processed by the invention.

"Organic nucleation center" refers to a simple or complex, non-synthetic species of organic molecule that is present, at least in part, as an undissolved solid in the form of nano- and/or microparticles. The subterm "nucleation center" is derived from the field of crystallography and describes a "seed" around which material accretes on the surface. Since most organic molecules manifest some degree of aqueous solubility, the necessity for an undissolved solid is satisfied by using an amount greater than necessary to saturate the solution. Non-limiting examples organic nucleation centers that are effective in supersaturating amounts particularly include highly polar species such as carbohydrates, ureides, amino acids, and potentially combinations thereof. Starch and cellulose are examples of carbohydrate organic nucleation centers. Uric acid and allantoin are examples of ureide organic nucleation centers.

"Organic solvent" refers to naturally occurring or synthetic organic compound existing in a liquid state. Examples suitable to practice the invention include but are not limited to ethylene glycol, propylene glycol, dimethyl sulfoxide, ethanol, and phenoxyethanol.

"Preferential exclusion" describes an interaction whereby certain dissolved substances are deficient in the immediate area surrounding a hydrophilic (hydrated) surface, in comparison to the concentration of the same substances in the bulk solution. Preferentially excluded solutes particularly include so-called precipitating salts, non-ionic polymers, and amino acids.

"Synthetic particles" may range in size from less than 100 nm to more than 100 microns. They may be porous or non-porous. They may polymeric, composed for example of polymethacrylates, polyacrylates, agarose, cellulose, dextran, or other polymers, or they may be inorganic, such as silica. They may be of uniform structure throughout, or they may be compound, consisting of an inner core of one material such as a metal alloy or hydrophobic polymer, and coated with an applied surface that is highly hydrated or permits the attachment of chemical groups to produce a highly hydrated surface. "Synthetic particles" may include particles designed for chromatographic applications, or particles intended for applications entirely distinct from the field of chromatography.

"Polynucleotide" refers to a biopolymer composed of multiple nucleotide monomers covalently bonded in a chain. DNA (deoxyribonucleic acid) and RNA (ribonucleic acid) are examples of polynucleotides.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Stem cells" refer to a class of cells known for their ability to differentiate into any type of tissue.

"Supersaturated starch" refers to a solution containing an amount of starch in excess of its maximum solubility under the conditions prevailing in a particular protein preparation. In certain embodiments, the invention provides a sample with starch present in an amount greater than such starch's solubility in such sample under the conditions for such sample such that some fraction of such starch is present in an undissolved form in the sample, such as, for example 10% starch, or 20% starch, or larger or lesser amount depending on the requirements for a particular application.

"Supersaturated ureide" refers to a solution containing an amount of ureide in excess of its maximum solubility under the conditions prevailing in a particular protein preparation. In certain embodiments, the invention provides a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the invention include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl)dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Tripartite system" or "3-phase system" refers to a system used to precipitate a target species that consists mainly of the aqueous preparation containing the target species, an organic nucleation center, and a preferentially excluded precipitating agent. One example would be a cell culture supernatant containing a monoclonal antibody, starch, and PEG.

"2-phase system" refers to a system which is distinct from 3-phase systems of certain embodiments of the invention and is used to precipitate a target species that consists mainly of the aqueous preparation containing the target species, and a preferentially excluded precipitating agent. One example would be a cell culture supernatant containing a monoclonal antibody, and ammonium sulfate.

"Ureide" refers to a cyclic or acyclic organic molecule of natural or synthetic origin that comprises one or more urea moieties or derivatives thereof. In certain embodiments, the invention provides ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), purines, and derivatives thereof. In certain embodiments, the invention provides organic molecules of the formula R—CO—NH—CO—NH$_2$ or R—CO—NH—CO—NH—CO—R or R'R"NH—CO—NR'"R"" where the relevant "R-groups" may be H or any organic moiety.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope. Examples include but are not limited to a dsDNA virus, a ssDNA virus, a dsRNA virus, a (+)ssRNA virus, a (−)ssRNA virus, a ssRNA RT virus and a dsDNA-RT virus; an adenovirus, a herpes virus, a poxvirus, a parvovirus, a reovirus, a picornavirus, a togavirus, an orthomyxovirus, a rhabdovirus, a retrovirus, a hepadanvirus, a papillomavirus, a Human Immunodeficiency Virus (HIV), an influenza virus, dengue virus, Japanese encephalitis virus, West Nile virus, and bacteriophages. The term virus is understood to include virus particles for use as vectors for gene therapy, for use as vaccines, and as replacements for antibiotics. It is also understood to include so-called pseudovirions, which may be described as virus particles that have been recombinantly modified to conserve their ability to generate protective immunity while eliminating their ability to cause infection.

"Von Willebrands Factor" is a clotting protein. It binds to Factor VIII, forming so-called anti-hemophiliac factor, with a molecular weight of about 2 million Daltons.

Details of Materials and Methods for Practice of Certain Embodiments

Effective materials for use as organic nucleation centers may consist of natural organic compounds present in an amount that is at least partly insoluble in the preparation. Examples include but are not limited to highly polar materials such as carbohydrates, including but not limited to cellulose, starch, and sugars; ureides, including but not limited to allantoin and uric acid; and amino acids, including but not limited to histidine. Materials that do not swell in water will generally be preferred, though materials that do swell, such as cellulose, do produce effective results. Performing the method will be simplified by using a single constraining agent, but combinations of two or more can be used effectively. As a general matter, the inherent affinity of the species to be precipitated for the organic nucleation center should be nil, since strong affinity may result in poor recovery of the target species upon elimination of the precipitating agent. Weak affinity however may enhance the purity achieved by the method, and recovery losses can be minimized by performing the recovery step in the presence of a substance that weakens or suspends the affinity factor. The use of ureides produces the surprising effect of aggregate reduction in antibody preparations, apparently due to their differential affinity for larger species over smaller species. This represents a profound distinction of the method from traditional methods that tend to preferentially enrich aggregates.

The physical form of the organic nucleation center may be particulate, filamentous, or branched filamentous. Particles of any granularity may be employed. Finer granularity translates to a higher surface area per dry gram, which can be expected to correspond with higher co-precipitating capacity per gram and favor the use of lower amounts of the nucleation center. Coarser granularity can be expected to yield the opposite trend but could be advantageous in some circumstances by facilitating supernatant removal by filtration rather than centrifugation. For applications using particulate materials, non-porous materials or materials with pores too small to permit entry of the target species will be preferred since this will avoid potential losses due to a proportion of the target species failing to exit the pores.

The quantity of the organic nucleation center should be of an amount sufficient to co-precipitate all of the target species. This can be determined easily by experimentation. Typical amounts of organic nucleation center may range from 5% to 20%, but the method can be practiced with lower and higher amounts without reducing its effectiveness. As a general matter, it will be prudent to use an amount moderately greater than the experimentally determined minimum in anticipation of lot-to-lot variations of the sample material. A so-called moderately greater amount might consist of 10% more, or 50% more, or twice the minimum amount, depending on the level of variation in sample composition. Much larger amounts may result in unacceptable loss of the target species.

The constraining agent may be any of the preferentially excluded solutes commonly used for precipitation of proteins and viruses, including but not limited to ammonium sulfate, sodium sulfate, sodium citrate, or potassium phosphate; or PEG, PPG, PVP, or dextran, among others. The method will generally be simpler if only a single constraining agent is employed, but it can be performed effectively with combinations of two or more. In general, the effective level of the chosen constraining agent will be similar to the level employed for precipitation absent the invention, but careful experimentation will usually reveal the necessary amount to be lower. Higher levels can nevertheless be used effectively, and may have the effect of reducing the necessary quantity of organic nucleation center, so long as the higher amount of constraining agent does not result in an unacceptable reduction of purification factor.

The constraining agent can be added as a liquid concentrate to increase the efficiency with which it is dispersed throughout the liquid. Addition may be performed manually or automated conveniently through the use of a pump. The constraining agent may alternatively be added as a powder. This offers the advantage of reducing the final process volume, but increases the time period over which addition must occur since time must be allowed to permit the constraining agent to dissolve. As a general starting point, addition of constraining agents as liquid concentrates may be performed over 30 minutes, while addition of dry powder may be performed over 60 minutes. Subsequent experimentation will reveal the specific limits for any given application.

A surprising and important feature of the invention is that nonionic-polymer constraining agents frequently give better results than precipitating salts. The use of precipitating salts results in the co-precipitation of small molecule contaminants including pH indicator dyes and other hydrophobic substances. The use of non-ionic polymer constraining agents avoids this, possibly because the hydrophobicity and strong hydrogen binding potential of nonionic polymers such as PEG enhance the solubility of those contaminants and discourage their non-specific interaction with the organic nucleation centers.

The method may be used for primary product capture, intermediate purification, or polishing; e.g. the method may be used before other purification methods, or after, in whatever sequence best serves the overall needs of the purification. Other purification methods may consist of other precipitation methods, though more likely chromatography methods, potentially including but not limited to affinity chromatography, anion exchange chromatography, cation exchange chromatography, hydrophobic interaction chromatography, so-called mixed mode chromatography methods.

Antibodies and virus particles represent two well-known classes of target species to which the method can be applied, but it can be used to achieve the same benefits with any target species that can be precipitated effectively with traditional 2-phase systems.

While the method will be used most frequently for co-precipitating the product of interest from an impure mixture, it may also be applied to co-precipitate a particular contaminant from a preparation while the product of interest remains soluble.

It is anticipated as a general matter that the uniformity of the organic nucleation centers will permit a significantly higher degree of resolution than can be obtained with traditional 2-phase systems. In other words, the invention will likely allow effective fractionation of the product of interest from contaminants that are not effectively fractionated by 2-phase systems.

Although the inclusion of organic nucleation centers will be of the greatest benefit in systems where precipitation is driven by preferentially excluded agents, it is anticipated that it will offer significant improvements with other precipitating agents, for example organic solvents.

Additional objects and advantages of the invention will be set forth in part in the description which follows, and in part will be obvious from the description, or may be learned by practice of the invention. The objects and advantages of the invention will be realized and attained by means of the elements and combinations specified in the claims.

It is to be understood that both the foregoing general description and the following detailed description are exemplary and explanatory only and are not restrictive of the invention, as claimed.

This technology employs insoluble but hydrated organic nucleation centers of size ranging from less than 100 nm to more than 100 µm. These nucleation centers particularly include natural organic materials, in contradistinction to synthetic particles designed or intended for practicing chromatography. Hydration is conferred by interaction of polar surface residues with water. Such particles are combined with a protein or other product of interest. The large total cumulative surface area of the organic nucleation centers favors a higher frequency of protein-surface interactions than protein-protein interactions. The subsequent addition of a non-ionic organic polymer such as polyethylene glycol (PEG) or other so-called excluded solute (constraining agent) causes a transfer of excess water from the interacting protein and surface to the bulk solvent, with the result that the protein is trapped on the surface. Untrapped contaminants are washed away. The association remains stable until the PEG is removed in a now-purified state by removal of the excluded solute.

The high availability of a hydrated surface favors rapid kinetics (seconds-minutes) which is highly advantageous over precipitation with excluded solutes (30 minutes to hours).

The uniformity of the hydrated surface favors narrowly defined adsorption and desorption isotherms in comparison to the usual broadly defined precipitation and resolubilization isotherms caused by interaction of protein-protein surfaces. This translates into higher resolution, e.g. higher purification factor.

The use of organic nucleation centers to enhance fractionation speed and resolution over traditional precipitation methods with excluded solutes such as nonionic organic polymers such as PEG, and precipitating salts such as ammonium sulfate, among others.

Constraining agents suitable for practicing the invention particularly include nonionic organic polymers such as polyethylene glycol (PEG), generally of a molecular weight ranging from 600 to 6000 Daltons, but also lower and higher molecular weights. Other nonionic organic polymers may be used effectively, such as but not limited to polypropylene glycol, dextran, and others. Other preferentially excluded agents suitable for practicing the invention may include kosmotropic salts from the group comprising ammonium sulfate, sodium sulfate, sodium or potassium citrate, potassium phosphate, and others; and amino acids such as glycine. Experimental data indicate that different preferentially excluded agents confer different selectivities. Thus it may be worthwhile to compare results achieved with excluded salts versus nonionic organic polymers or amino acids, though as a general matter the best results are obtained with nonionic organic polymers, especially when the biological sample is of crude composition such as a cell culture supernatant. The use of preferentially excluded salts with such samples usually suffers from the accretion on the chromatography support of highly colored hydrophobic substances that can create runaway increases in operating pressure. The use of nonionic organic polymers as the preferentially excluded agent generally prevents this problem, apparently because of the inherent hydrophobicity of such polymers. Although the method may be practiced with combinations of different classes of preferentially excluded agents, such as salts with nonionic organic polymers, care must be exercised since some combinations create spontaneous phase separations. Another valuable benefit of nonionic organic polymers is their chemical gentleness. High concentrations of PEG have a long-standing reputation for stabilizing proteins, they are well tolerated by living cells, and many FDA-approved human-injectable therapeutic formulations employ PEG as an inactive ingredient.

Chromatography supports suitable for practicing the invention particularly include media with surfaces that are highly hydrated. Many polymer-based media unfunctionalized for adsorption chromatography have surfaces that are densely populated by hydroxyl groups that interact strongly with water, leaving the surface highly hydrated. Surfaces that have been functionalized with highly hydrated materials are also ideal, potentially including immobilized sugars, starch, other carbohydrates, and ureides. Positively and negatively charged groups also tend to be highly hydrated, and can be used to practice the invention at high salt conditions where charge interactions between biological sample components and the support are effectively suspended. Surfaces with some hydrophobic character may be suitable if they possess an overall polar character sufficient to dominate the surface, which will exclude most surfaces intended for conducting hydrophobic interaction chromatography. Although particle-based chromatography supports may be used with adequate efficiency to demonstrate proof of principle, the method works so marginally as prohibit it practical use. Useful capacity and fractionation ability at high flow rates are achieved only with convective chromatography supports such as monoliths and membranes. Monoliths will generally support higher capacity and resolution than membranes, while membranes will generally support higher flow rates than monoliths. Which best suits the needs of a particular application can be determined by simple experimentation.

Biological products that can be effectively purified with the invention include proteins including antibodies and clotting factors; virus particles; cellular organelles such as ribosomes, mitochondria, and exosomes, among others.

Elution of biological products bound to a support may be achieved by adding an agent that interferes with the ability of the preferentially excluded agent to maintain binding of the target product. Such agents include preferentially surfactants, urea, neutral salts, polysaccharides, and chaotropic salts such as sodium or potassium thiocyanate, sodium or potassium perchlorate and guanidine; or such agents can be applied in conjunction with reducing the concentration of the preferentially excluded agent, though in most cases the simple method of reducing the preferentially excluded agent will be preferred.

Although chemical interactions other than the sharing of hydration water between the chromatography surface and the product of interest are understood to be nil, the selectivity and efficiency of the method is significantly affected by pH and conductivity. This is consistent with expectations since pH will affect the surface charge of the product, which will in turn affect its degree of hydration. The effect of conductivity is not fully understood at present, but from a practical perspective, inclusion of significant concentrations of sodium chloride frequently have the general effect of reducing operating pressure, and permitting the column to be loaded to higher capacities. This is noteworthy because it is contrary to behavior of both ion exchange and hydrophobic interaction chromatography, thereby highlighting the unique selectivity of the method. As a general matter, selectivity is dominantly a function of the size of the product of interest, with the strength of retention increasing in proportion to the size of the product. This is consistent with the fact that protein hydration is proportional to size. A practical consequence is that the concentration of preferentially excluded agents required to achieve binding is inversely proportional to product size. Good virus binding is achieved at PEG-6000 concentrations as low as 5%, while IgM antibodies require twice that, and IgG antibodies another 5% more.

An additional benefit to the use of nonionic organic polymers is that it offers direct compatibility with other chromatography methods that might be used to increase the degree of purification following use of the invention. PEG is nonionic, and thus avoids interference with non-hydrophobic ligand-based chromatography methods. Experimental results have established that antibodies and virus particles purified by the method may be applied directly to anion exchangers and hydroxyapatite columns, in both cases without requirement for intermediate equilibration of the sample. This highlights the point that the invention can be practiced in combination with one or more other methods, generally including other chromatographic methods, precipitation methods, and methods of liquid-liquid partitioning. It is within the ability of a person of ordinary skill in the art to develop appropriate conditions for these methods and integrate them with the invention described herein to achieve the desired purification of a particular biological product.

In preparation for contacting a sample containing a target species with a highly hydrated chromatography surface, it can be desirable in certain embodiment to equilibrate the chemical environment inside the chromatography support. This can be accomplished by flowing an equilibration buffer through the column to establish the appropriate conditions, particularly including the concentration the preferentially excluded solute. In certain embodiments, the equilibration buffer may include a buffering compound to confer adequate pH control. Such compounds include but are not limited to acetate, phosphate, citrate, MES, HEPES, BICINE, imidazole, and Tris. The pH of the equilibration buffer may range from about pH 4.0 to about pH 9.0. In one embodiment suitable for the purification of monoclonal IgM, the equilibration buffer contains Hepes at a concentration of about 50 mM at a pH of 7.0, sodium chloride and a concentration of 200 mM, plus PEG-6000 at a concentration of 12.5%. In another embodiment suitable for the purification of IgG, the equilibration buffer contains Hepes at a concentration of about 50 mM at a pH of about 7.0, sodium chloride at a concentration of 1.0 M, plus PEG-6000 at a concentration of 15%. In another embodiment suitable for the purification of a virus particle, the equilibration buffer contains MES at a concentration of about 50 mM at a pH of 5.8, sodium chloride at a concentration of 600 mM, and PEG-6000 at a concentration of 6%. In another embodiment suitable for purification of an antibody, the equilibration buffer contains Hepes at a concentration of about 50 mM at a pH of about 7.0, and ammonium sulfate at a concentration of about 1.5 M.

In certain embodiments the product preparation is equilibrated to conditions compatible with the column equilibration buffer before the invention is practiced. In one embodiment, the sample may be pumped onto the column through one line, a concentrated solution of the preferentially excluded solute pumped onto the column simultaneously through another line, and the two lines mixed immediately before the column to minimize the precolumn time interval during which the product is exposed to the preferentially excluded agent, as a means of limiting the degree of precipitation that may occur before the sample flows onto the column. In one embodiment, the concentration of the preferentially excluded agent being applied through one line is 125% of the target concentration of the mix, and the mixing ratio of preferentially excluded agent to sample is 80% agent, 20% sample. In certain embodiments, this provides a broadly effective starting point, with the only necessity being to determine the amount of preferentially excluded agent required in the final mix to achieve the desired product binding characteristics. With a working method in hand, the relative concentration of the preferentially excluded agent and the proportioning factor may be varied to identify the conditions that support that highest capacity in combination with the lowest mixed sample volume.

In certain embodiments, the preferentially excluded agent is PEG-8000, or PEG-6000, or PEG-3500, or PEG-2000, or PEG-1000, or PEG-600. As a general matter, the larger the polymer, the lower the concentration required to achieve good binding. Since lower molecular weight PEGs tend to have disproportionately lower viscosity. Since lower viscosity will generally be beneficial in generating lower operating pressure and exerting less stress on the mixing capabilities of the mechanical system, it will be worthwhile to explore this option.

In certain embodiments, the formulation of the equilibration buffer may be substantially different from the formulation of the equilibrated sample. For example a 1.2 M sodium chloride might be added to the sample, while the equilibration buffer contains only 200 mM sodium chloride with the objective of maintaining a net sample salt concentration of 400 mM sodium chloride (in-line dilution proportion 80:20), then washing immediately thereafter with 200 mM sodium chloride. Such a tactic might be used when the higher salt concentration was due to higher capacity binding but the lower salt concentration was more effective for washing away a particular subset of contaminants. Besides differing with respect to salt concentration, the two buffers might also differ with respect to pH or the presence, absence, or amounts of other agents. A similar effect could be accomplished by optionally applying a second wash buffer.

In certain embodiments of the invention, the column is washed following sample loading, by a wash buffer, usually of the same composition as the equilibration buffer, to remove unbound contaminants from the chromatography support.

In certain embodiments of the method, the product is then eluted from the chromatography support solely by reducing the concentration of the preferentially excluded agent, for example by creating a gradient from Hepes/PEG to just Hepes buffer.

In another embodiment, the reduction of the preferentially excluded agent is accompanied by an increase of one or more elution enhancing substances by including such substances in the gradient end-point buffer. Examples of such agents might include, urea, arginine, or a surfactant, among others.

Constraining agents suitable for practicing certain embodiments of the invention particularly include nonionic organic polymers such as polyethylene glycol (PEG), generally of a molecular weight ranging from 600 to 6000 Daltons, but also lower and higher molecular weights. High concentrations of PEG have a long-standing reputation for stabilizing proteins, they are well tolerated by living cells, and many FDA-approved human-injectable therapeutic formulations employ PEG as an inactive ingredient. Other nonionic organic polymers may be used effectively, such as but not limited to polypropylene glycol, dextran, and others. Other preferentially excluded agents suitable for practicing the invention may include kosmotropic salts from the group comprising ammonium sulfate, sodium sulfate, sodium or potassium citrate, potassium phosphate, and others; and amino acids such as glycine. Experimental data indicate that different preferentially excluded agents confer different selectivities. Thus it may be worthwhile to compare results achieved with excluded salts versus nonionic organic polymers or amino acids. The method may be practiced with combinations of different classes of preferentially excluded agents, such as salts with nonionic organic polymers, but care must be exercised since some combinations will create spontaneous phase separations.

Chromatography particles suitable for practicing certain embodiments of the invention particularly include particles with surfaces that are highly hydrated. Many polymer-based media unfunctionalized for adsorption chromatography have surfaces that are densely populated by hydroxyl groups that interact strongly with water, leaving the surface highly hydrated. Surfaces that have been functionalized with highly hydrated materials are also ideal, potentially including immobilized sugars, starch, other carbohydrates, and ureides. Positively and negatively charged groups also tend to be highly hydrated, and can be used to practice the invention at high salt conditions where charge interactions between biological sample components and the support are effectively suspended. Surfaces with some hydrophobic character may be suitable if they possess an overall polar character sufficient to dominate the surface, which will exclude most surfaces intended for conducting hydrophobic interaction chromatography.

The method of certain embodiments can be practiced with porous particles but non-porous particles have proven to be advantageous. Porous particles offer the potential for various proteins, including both the contaminants and the product of interest, to diffuse into the pores, and then gradually leak out at various stages of the process, compromising purity or product recovery, or both.

In certain embodiments, particles may range in size from less than 100 nm to more than 200 μm. This covers the range from nanoparticles to microparticles, both of which have been shown to be effective. Particles may be composed any material, including polymers, minerals, or metals, any of which may be of compound structure with a surface composition different from the interior of the particles. This particularly includes iron-core particles designed to be collected by magnetic separators, and alloy core particles where the core is present to create high density when the method is practiced in a so-called expanded bed mode. An example of the latter might include, for example tungsten-carbide-core particles coated with cellulose.

In certain embodiments, the quantity of particles should be of an amount sufficient to accommodate binding of all of the target species. This can be determined easily by experimentation. Typical amounts may range from 5% to 20%, but the method can be practiced with lower and higher amounts without reducing its effectiveness. As a general matter, it will be prudent to use an amount moderately greater than the experimentally determined minimum in anticipation of lot-to-lot variations of the sample material. A so-called moderately greater amount might consist of 10% more, or 50% more, or twice the minimum amount, depending on the level of variation in sample composition. Much larger amounts may result in unacceptable loss of the target species.

In certain embodiments, the constraining agent can be added as a liquid concentrate to increase the efficiency with which it is dispersed throughout the liquid. Addition may be performed manually or automated conveniently through the use of a pump. The precipitating agent may alternatively be added as a powder. This offers the advantage of reducing the final process volume, but increases the time period over which addition must occur since time must be allowed to permit the precipitating agent to dissolve. As a general starting point, addition of precipitating agents as liquid concentrates may be performed over 30 minutes or more, while addition of dry powder may be performed over 60 minutes or more. Subsequent experimentation will reveal the specific limits for any given application.

Biological products that can be effectively purified with the certain embodiments of the invention include proteins including antibodies and clotting factors; virus particles; cellular organelles such as ribosomes, mitochondria, and exosomes, among others. At a more general level, the invention can be applied to advantage for the purification of any product that may be partially purified by precipitation with either salts or nonionic organic polymers.

While the method of certain embodiments of the invention will be used most frequently for precipitating the product of interest from an impure mixture, it may also be applied to precipitate a particular contaminant from a preparation while the product of interest remains soluble.

The invention can be practiced with mechanical systems ranging from very simple to very complex, without departing from its essential features.

In order to practice certain embodiments of the invention as they relate to co-precipitation methods, it will be useful to have a defined starting point from which to measure its benefits. One way to approach this is to begin by performing ammonium sulfate precipitation and/or PEG precipitation according to standard protocols to produce reference material. Then perform the salt and/or PEG counterparts of the invention. For example, in the case of an IgG antibody, combine the antibody preparation with starch at a weight-to-volume proportion of 20%. With the starch thoroughly dispersed (stirring) in the antibody preparation, add 30% PEG-6000 over a period of 30 minutes to a final concentration of 15% PEG. Centrifuge the sample to sediment the starch and co-precipitated antibody. Recover the antibody by resuspending the co-precipitate mixture with a physiological buffer such as phosphate buffered or Hepes buffered saline (100-150 mM NaCl), pH 6.8-7.2. In the case of IgM, a lower amount of PEG will usually suffice, such as 12.5%. With virus species, a much lower amount of PEG will usually suffice, such as 5-7.5% PEG. Characterize purity, recovery, and aggregate content by standard laboratory methods.

In addition to PEG usually giving better results than precipitating salts, it offers in certain embodiments broader opportunities to fine-tune the selectivity of the method to optimize purity and recovery. The high conductivity of precipitating salts suppresses charge interactions among proteins, which makes it impossible to explore the effects of low conductivity and makes the behavior of the system less responsive to changes in pH. With PEG, conductivity can be varied from nil to very high with non-precipitating salts such as sodium chloride. At low conductivity values in particular, variations in pH may offer significant opportunities to alter the selectivity of the system.

In certain embodiments, it will generally be worthwhile to explore differences in results with carbohydrate organic nucleation centers, versus ureide organic nucleation centers. For example, by simply substituting allantoin for starch and comparing results, paying particular attention to the aggregate content of the recovered protein, permits assessment of the relative merits of certain organic nucleation centers in certain embodiments of the invention. Antibody recovered from the ureide version of the invention frequently contains 1-2% lower aggregates. Ureides may tend to give lower recoveries than starch with viruses due to weak binding of some proteins, but the effect can be compensated by including arginine or urea in the buffer in which co-precipitation is performed. Following basic evaluation of starch versus allantoin, it may be worthwhile to evaluate results with a broader selection of both classes.

With the organic nucleation center, precipitating agent, pH and conductivity conditions defined, experiments may be performed to determine the needed amount of organic nucleation center per volume of sample. In certain embodiments, the 20% amount suggested above will generally prove excessive. Larger amounts can be evaluated, but smaller amounts will usually prove adequate. As a general matter, smaller amounts will prove advantageous especially if the method is intended to be scaled up.

Irrespective of the materials and proportions, the purity of the final product can generally be improved in certain embodiments by conducting an intermediate wash step between the initial co-precipitation and the recovery step. This wash step may consist of resuspending the first co-precipitate with a clean solution of buffer containing the same concentration of precipitating agent as the original co-precipitation mixture, then discarding the second supernatant. This operation dilutes contaminants that may remain in the fluid in the interstices of the co-precipitate after the initial precipitation. This step may be repeated if desired to produce yet higher levels of purity. This may be facilitated by conducting the wash in a filtration format instead of by centrifugation.

Irrespective of the materials and proportions, in certain embodiments the recovery of the final product can generally be improved by conducting a second recovery step. After removing the initial recovery buffer containing the re-solubilized product, another aliquot of clean buffer may be added to resuspend the organic nucleation center. This allows recovery of resolubilized product that may have been inaccessible in the interstices of the organic nucleation center after the first recovery step.

As suggested at various points in the foregoing discussion, in certain embodiments the method can be conducted in either a centrifugation or a filtration format.

In some embodiments, the invention provides a method for purification of large biological compounds that are believed to work, without being bound by any specific theory, by trapping them at a non-reactive hydrophilic surface, exclusively through constrained sharing of water between their respective hydration shells. Entrapment is induced and stabilized by agents such as polyethylene glycol (PEG) that preferentially hydrate hydrophilic surfaces. Selectivity correlates with molecular size. Retention increases with PEG size and concentration. Binding is enhanced near the isoelectric point (pI) of the target biomolecule. Salt weakens retention by reducing PEG size. Single-step purification factors from crude feed streams range from more than 90% for IgG to 99.8% for virus particles. Near-physiological pH and conductivity fractionation conserves activity of chronically labile biologicals such as virus and IgM. Virus binding capacity on monoliths is about 1 trillion particles per mL. A magnetic nanoparticle-based version achieves 30-fold higher IgG binding capacity than the corresponding cation exchange particles.

It will be apparent to the person of ordinary skill in the art how to scale the process up to the degree necessary to support a given application.

EXAMPLES

Example 1

Purification of IgM. 100 mL of clarified cell culture supernatant containing about 50 μg/mL IgM clone 529 was set stirring. 4 g of potato starch was dispersed in the solution. 30% PEG-6000 in 50 mM Hepes, 200 mM NaCl, pH 7.0 was added through a peristaltic pump to a final concentration of 10% over a period of 30 minutes. Stirring was continued for an additional 30 minutes followed by centrifugation and removal of the supernatant. The co-precipitated IgM-starch was washed by resuspension in 10% PEG 50 mM Hepes, 200 mM NaCl, pH 7.0, then centrifuged, and the supernatant removed. The IgM was dissociated and recovered from the starch by addition of 50 mL of 50 mM Hepes, 200 mM NaCl, pH 7.0. Samples from selected steps in the process were analyzed by size exclusion chromatography. The majority of host proteins and cell culture components were found in the first supernatant. About 90% pure IgM was found in the recovered fraction, with a recovery of about 70%. The experiment was repeated with starch from rice and from corn. IgM recovered from corn and rice starch had slightly more host protein contamination, and rice had more high molecular weight aggregates.

Example 2

Purification of IgG. 100 mL of cell culture supernatant containing about 800 µg/mL IgG clone her2 was set stirring. 2 g of potato starch was dispersed in the solution. 30% PEG-6000 in 50 mM Hepes, 200 mM NaCl, pH 7.0 was added through a peristaltic pump to a final concentration of 15% over a period of 30 minutes. Stirring was continued for an additional 30 minutes followed by centrifugation and removal of the supernatant. The co-precipitated IgG-starch was washed by resuspension in 15% PEG 50 mM Hepes, 200 mM NaCl, pH 7.0, then centrifuged, and the supernatant removed. The IgG was dissociated and recovered from the starch by addition of 50 mL of 50 mM Hepes, 200 mM NaCl, pH 7.0. Another 100 mLs of supernatant was precipitated by PEG in the absence of starch, using the same solutions and endpoints. Samples of the recovered antibody were analyzed by size exclusion chromatography. IgG recovered from both methods contained about 2% aggregate. Comparison with ammonium sulfate produced the same result. The experiment was repeated, substituting allantoin for potato starch. IgG recovered from co-precipitation with allantoin contained about 0.2% aggregate, a reduction of about 10-fold over the other methods. Subsequent treatment of the allantoin with 200 mM arginine released a highly aggregated fraction of IgG. Related experiments with IgM revealed the same trend. IgM recovery was 75% with 20 g/L allantoin, 55% with 40 g/L. These result show that allantoin preferentially retains larger molecular weight species. They also suggest that allantoin may have an aggregation-suppressive effect, possibly mediated by the mildly reducing redox character of its surface.

Example 3

Purification IgM. Three dilutions of IgM cell culture supernatant were prepared: 1×, 2×, 4×. 4 grams of potato starch was added to 100 mL of each solution and co-precipitated with 10% PEG-6000 (50 mM Hepes, 100 mM NaCl, pH 7.0 diluent). Antibody recovery was about 80% the two lower dilutions, but only 25% from the 4-fold dilution.

Example 4

Purification of virus. A series of experiments was conducted on a sample of *E. coli* cell culture supernatant containing bacteriophage M13. The conditions of example 1 were repeated except at PEG concentrations of 4% and 8% PEG-6000. Analytical anion exchange chromatography revealed that all preparations produced phage of about 90% purity. Recovery was estimated at 75% with 8% PEG, but less than 25% at 4% PEG. Another series of experiments was conducted with 30%, and 40% starch at 6% PEG. Recovery was about 80% at 30% starch, and at least 90% at 40% starch. Another series of experiments was conducted at 6% PEG, 20% starch, but 400, 600, and 800 mM NaCl. Recovery was estimated to be at least 90% at salt concentrations of 600 mM and above 600 mM NaCl. Another series of experiments was conducted at 6% PEG, 20% starch, 600 mM NaCl but at pH values of 5, 6, 7, 8, and 9. Recovery was estimated to be at least 90% at pH 6 and below, and declined with increasing pH. Final operating conditions of 40% starch, 6% PEG, 600 mM NaCl, pH 6.0 produced 90% purity and 90% recovery.

Example 5

A series of experiments was performed in which the binding characteristics of a purified IgM monoclonal antibody with an isoelectric point of about 5.5 were evaluated at different pH values and different concentrations of PEG-6000. All these experiments were conducted with a 334 µL OH monolith at a flow rate of 4 mL/min. Results are shown in FIG. 1. 100% binding of the IgM was achieved in 10% PEG at pH 5.0. FIG. 1 shows that pH of 9.5 may have been adequate to achieve 100% binding. 100% binding was achieved at 11% PEG at pH 6.0, and 12% PEG at pH 7.0. These results indicate that binding is strongest near the isoelectric point of a species. The experiment was repeated with an IgM with an isoelectric point above 9.0, and another with an isoelectric point estimated at about 7.0. In both cases, the strongest binding was observed under the lowest pH conditions. This example suggests that as with IgG, solubility of IgM is lowest at low pH regardless of isoelectric point. In cases where the isoelectric point of the IgM is also at low pH, then the pattern shown in the graph will be observed.

Example 6

Figure 2:
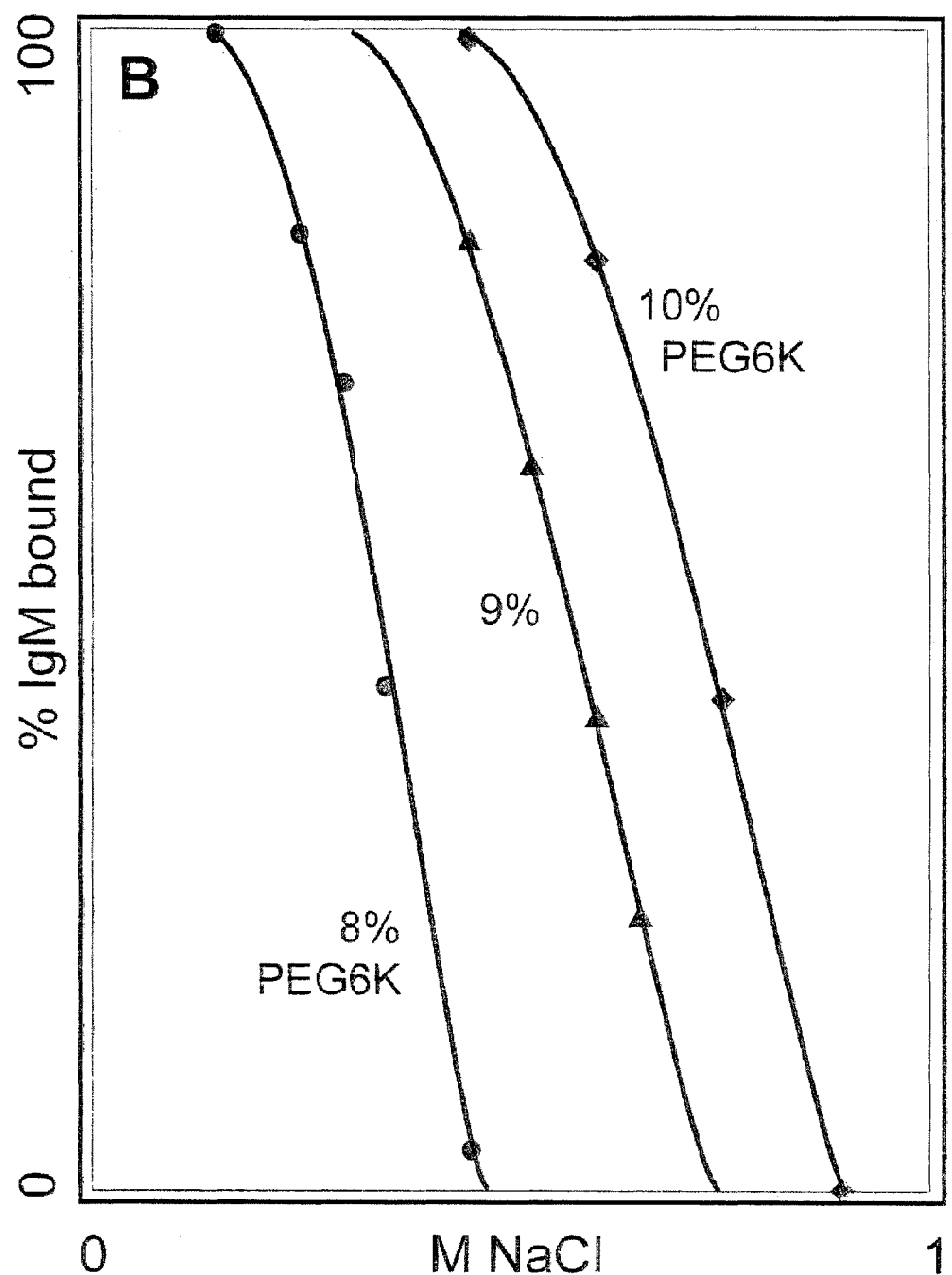
FIG. 2 shows the relationship between the percentage of IgM retained by constrained co-hydration at the surface of a hydrated monolith and concentration of NaCl for different percentages of the preferentially excluded agent, PEG-6000 (8%, 9%, 10%) as described in Example 6.

A series of experiments was performed in which the binding characteristics of an IgM were evaluated as a function of NaCl concentration. All experiments were conducted with PEG-6000 on a 334 µL OH monolith at a flow rate of 4 mL/min. Results are shown in FIG. 2. Binding efficiency was reduced dramatically with increasing salt concentration, requiring an increase in PEG-6000 concentration to achieve binding at higher salt concentrations. Experiments were conducted with different species of salt, for example ammonium sulfate and sodium thiocyanate. Thiocyanate had roughly the same effect as NaCl, while ammonium sulfate had a much greater effect on binding than NaCl. These results collectively suggest that the effect of salt is to compact the effective size of the PEG.

Example 7

Figure 3:
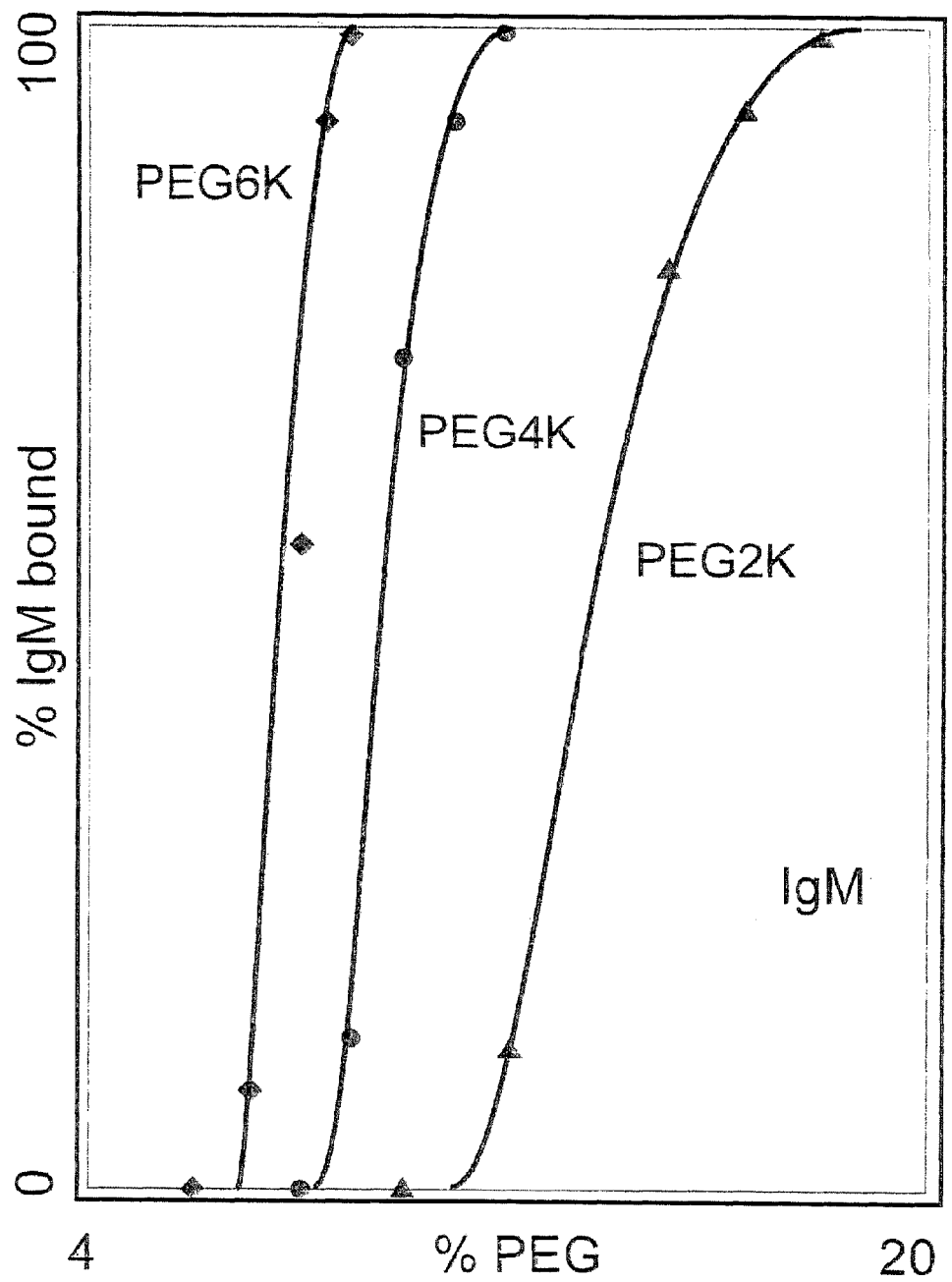
FIG. 3 shows the relationship between the percentage of IgM retained by constrained co-hydration at the surface of a hydrated monolith and percentages of a preferentially excluded agent, PEG of varying molecular weights (6000, 4000, and 2000) as described in Example 7.
Figure 4:
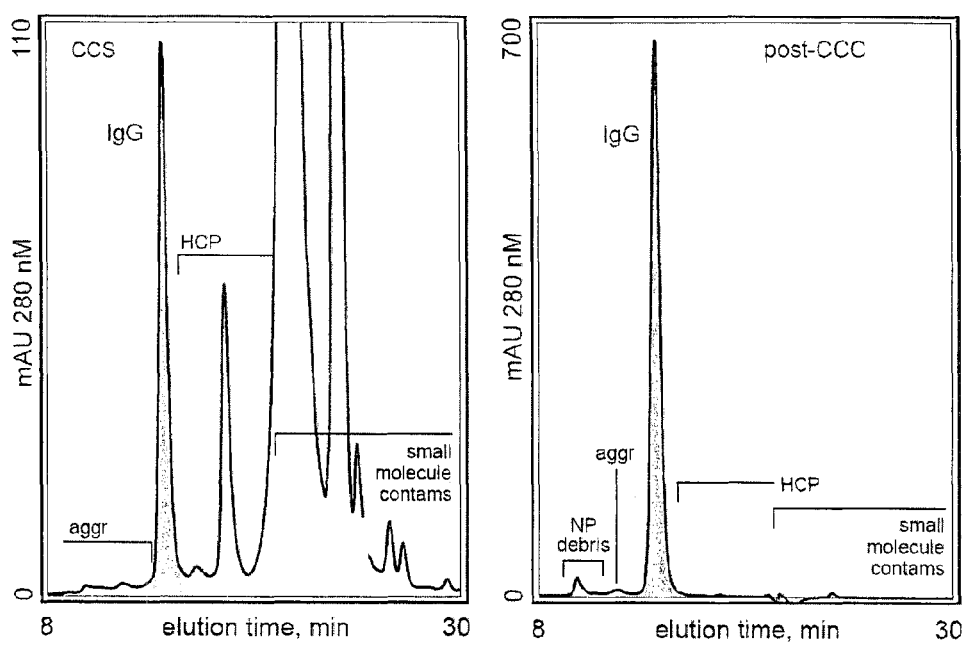
FIG. 4 shows the effectiveness of constrained cohydration with organic nucleation centers in the presence of PEG-6000 for purification of IgG as described in Example 8.

The effect of PEG size. A series of experiments in which IgM binding was evaluated as a function of PEG size. All experiments were conducted on a 334 µL OH monolith at a flow rate of 4 mL/min. Results are shown in FIG. 3, showing that larger PEGs are able to achieve binding at lower concentrations.

Example 8

Purification of monoclonal IgG by constrained cohydration on starch-modified magnetic nanoparticles. IgG-containing cell culture supernatant was combined with starch-modified magnetic particles. 50% PEG-6000 in 50 mM Hepes, 50 mM NaCl, pH 7.0 was infused by a peristaltic pump over a period of 30 minutes to a final concentration of 15% PEG, then the particles were captured in a magnetic field and the supernatant removed. The particles were washed by redispersing them in 15% PEG-6000, 50 mM Hepes, 50 mM NaCl, pH 7.0, then collecting them again in the magnetic field and removing the supernatant. The particles were redispersed in 5 particle volumes of 50 mM Hepes, 50 mM NaCl, pH 7.0, the particles were collected in a magnetic field, and the IgG containing supernatant was recovered. Example 4 illustrates the degree of purification obtained by this process. Recovery was estimated at 90%. A series of additional experiments revealed that 90% recovery and similar purification performance could be obtained at capacities about 30 times higher than protein A affinity nanoparticles of the same composition. These result were interpreted to reveal that constrained cohydration chromatography permits the accumulation of multiple product layers on the surface of nanoparticles whereas traditional adsorptive nanoparticles permit only the binding of a monolayer of antibody.

Example 9

Figure 5:
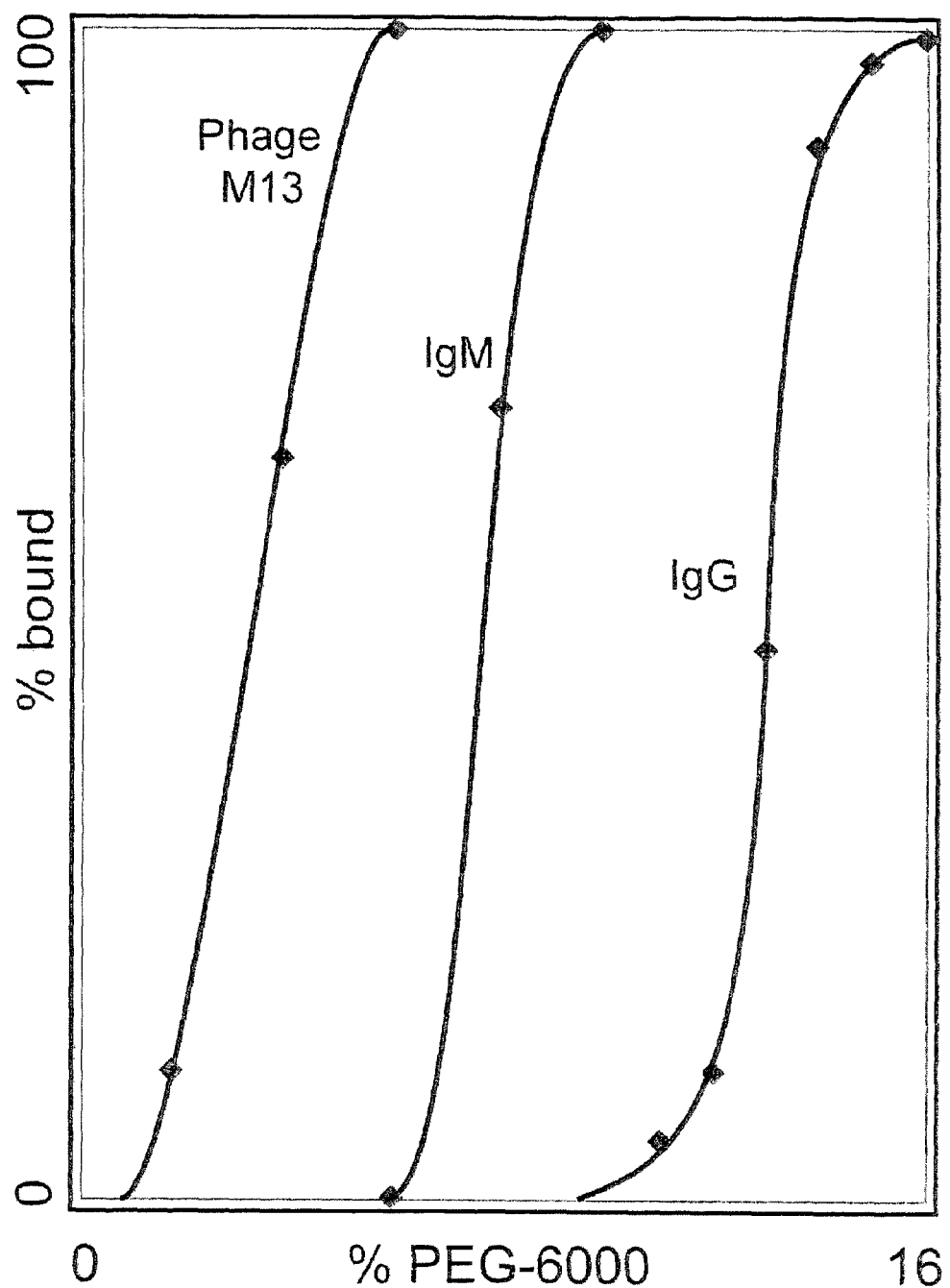
FIG. 5 shows the relationship between the percentage of a target species retained by constrained co-hydration at the surface of a hydrated monolith and percentages of a preferentially excluded agent PEG-6000 for three target species (Phage M13, IgM, and IgG) as described in Example 9.

The effect of PEG concentration. A series of experiments were conducted with virus (mass 16.7 MDa), IgM (mass 960 kDa), IgG (mass 160 kDa), and bovine serum albumin (BSA, mass 67 kDa) at various PEG concentrations to evaluate the relative contribution of biomolecule size. All experiments were conducted with PEG-6000 on a 334 µL OH monolith. Results are shown in FIG. 5. The species with the largest mass bound at the lowest PEG concentration, with smaller species requiring higher PEG concentrations to achieve equivalent binding. BSA barely began to bind at 15% PEG-6000. These results highlight the size selectivity of the technique. Parallel experiments conducted using insoluble starch or allantoin as a substrate in place of an OH monolith have shown that the same relationship persists regardless of which highly hydrated (hydrophilic) substrate is employed.

Example 10

Dynamic binding capacity of IgM. Dynamic binding capacity of an IgM monoclonal antibody was determined by feeding IgM at a constant concentration at 12% PEG, until IgM began to flow through the 334 µL OH monolith column as indicated by an increase in UV absorbance. This occurred at the point at which 39 mg of IgM had been loaded. Earlier experiments with other IgMs under various conditions indicated dynamic binding capacities generally in excess of 20 mg/mL.

Example 11

Dynamic binding capacity of virus. Dynamic binding capacity of bacteriophage M13 was determined by feeding phage at a constant concentration at 6% PEG, until phage began to flow through the 334 µL OH monolith column as indicated by an increase in UV absorbance. This occurred at the point at which $9.9 \times 10e12$ virus particles had been loaded.

Example 12

Conservation of virus infectivity. Bateriophage M13 purified by constrained co-hydration chromatography on an OH monolith in 6% PEG-6000 was compared to unpurified phage to measure relative biological activity. Infectivity of the purified phage was about 95%. In the context of the error factor inherent in this type of assay, it is understood that this most likely reflects complete conservation of viral activity.

Example 13

Binding efficiency and recovery of virus. Analysis by infectivity and chromatography indicate that constrained co-hydration chromatography of bacteriophage M13 as described above achieved more than 90% binding efficiency from crude unpurified feed stream, and that essentially all of that was recovered in the eluate.

Example 14

Purification efficiency of virus Analysis by ELISA for *E. coli* host proteins indicated that purification by constrained co-hydration chromatography removed 99.8% of the protein contaminants from bacteriophage M 13 in this single purification step. Subsequent purification by a follow-on anion exchange chromatography step reduced host cell protein by a combined total of 99.99%. AccuBlue assays showed that constrained cohydration chromatography removed more than 90% of DNA, and the subsequent anion exchange step reduced it by another 10 fold.

Example 15

Purification of monoclonal IgG. A 0.34 mL hydroxyl monolith with an average channel size of about 2 microns was attached to a chromatograph. It was equilibrated with a solution of 50 mM Hepes, 300 mM sodium chloride, 15% PEG-6000, pH 7.0 at a flow rate of 4 mL/min. 125 mL of sample was then fed to the column by inline dilution, 20% sample, 80% diluent buffer to produce final PEG concentration of 15%. After loading was completed, the bed was washed with equilibration buffer to remove unbound contaminants. The bed was then eluted with a reducing PEG gradient. The IgG eluted in the last quarter of the gradient. Analytical size exclusion chromatography showed that the antibody was greater than 95% pure with aggregate content similar to reference IgG purified by protein A affinity chromatography.

Example 16

Comparison of different highly-hydrated monoliths with monoclonal IgM. In separate experiments, 0.34 mL monoliths coated with hydroxyl groups, cation exchange groups (SO3), and anion exchange groups (QA) were compared. Each was equilibrated with a solution of 50 mM Hepes, 1 M sodium chloride, 12.5% PEG-6000, pH 7.0 at a flow rate of 4 mL/min. 125 mL of sample was then fed to the column by inline dilution, 20% sample, 80% diluent buffer to produce final PEG concentration of 12.5%. After loading was completed, the bed was washed with equilibration buffer to remove unbound contaminants. The bed was then eluted with a reducing PEG gradient. The endpoint buffer also contained 1 M NaCl so that salt concentration would be level throughout the experiments, thereby cancelling out the effects of charge interactions.

Example 17

Purification of monoclonal IgM from cell culture supernatant (clone A3, 20 µg/mL IgM, supplemented with 20% serum). An 8 mL hydroxyl monolith with an average channel size of about 2 microns was attached to a chromatograph. It was equilibrated with a solution of 50 mM Hepes, 300 mM sodium chloride, 12.5% PEG-6000, pH 7.0 at a flow rate of 75 mL/min. 1250 mL of IgM-containing cell culture supernatant was then fed to the column by in-line dilution, 20% sample, 80% diluent buffer to produce final PEG concentration of 12.5%. After loading was completed, the bed was washed with equilibration buffer to remove unbound contaminants. The bed was then eluted with a reducing PEG gradient. The IgM eluted in the last quarter of the gradient. Analytical size exclusion chromatography showed that the antibody was greater than 95% pure, with a recovery of 63%.

Example 18

Purification of monoclonal IgM from cell culture supernatant. An 8 mL hydroxyl monolith with an average channel size of about 2 microns was attached to a chromatograph. It was equilibrated with a solution of 50 mM Hepes, 300 mM sodium chloride, 12.5% PEG-6000, pH 7.0 at a flow rate of 75 mL/min. 1250 mL of a different IgM-containing cell culture supernatant was then fed to the column by in-line dilution, 20% sample, 80% diluent buffer to produce final PEG concentration of 12.5%. After loading was completed, the bed was washed with equilibration buffer to remove unbound contaminants. The bed was then eluted with a reducing PEG gradient. The IgM eluted in the last quarter of the gradient. Analytical size exclusion chromatography showed that the antibody was greater than 95% pure. The IgM fraction was the applied to a 10 mL column of hydroxyapatite (CHT type II, 40 micron) and eluted with a linear gradient to 300 mM sodium phosphate. The IgM fraction was diluted 1:1 with water and loaded onto an 8 mL QA anion exchange monolith in 50 mM Hepes, pH 7.0, at a flow rate of 75 mL/min, then eluted with a 10 column volume linear gradient to 300 mM sodium chloride in 50 mM Hepes, pH 7.0. Analytical size exclusion chromatography indicated that the 3-step process supported an overall recovery of 60% while producing greater than 99% pure IgM without detectable aggregates or fragments. This example demonstrates the integration of the invention with other purification methods to create a complete purification process. The experiment was repeated at 200 mM NaCl. Recovery and purity were essentially unchanged in comparison with 300 mM.

Example 19

Fractionation of fibrinogen. A 0.34 mL hydroxyl monolith was equilibrated with 50 mM Hepes, 2.0 M glycine, 10 mM EDTA, pH 7.0. 125 mL of partially purified human fibrinogen was fed to the column by in-line dilution, 20% sample, 80% diluent buffer to produce a final glycine concentration of 2.0 M. Some contaminants flowed through the column during sample application. After loading was completed, the bed was washed with equilibration buffer to remove unbound contaminants. The bed was then eluted with a reducing glycine gradient, producing a broad heterogeneous fibrinogen peak. Operating pressure increased during the run, but the effect was reversed by washing the column with 3 M guanidine.

Example 20

Purification of antihemophiliac factor (Factor VIII-vWF complex). A 0.34 mL hydroxyl monolith was equilibrated with 8% PEG-6000, 50 mM Hepes, 200 mM NaCl, pH 7.0. A mixture of antihemophiliac factor in human serum albumin (HSA) was applied at the same concentration of PEG-6000. HSA failed to bind and was eliminated during loading. The column was washed briefly with equilibration buffer and the antihemophiliac factor eluted in a 10 mL linear gradient to 50 mM Hepes, 200 mM NaCl, pH 7.0.

Example 21

Virus purification. And 1 mL OH-monolith was equilibrated to 6% PEG-6000, 50 mM Hepes, 600 mM NaCl, pH 7.0. This was done by equilibrating with an 50:50 mixture of 12% PEG-6000, 50 mM Hepes, 600 mM NaCl, pH 7.0 to 50 mM Hepes, 600 mM NaCl, pH 7.0. 100 mL of bacteriophage M13 was loaded by in-line dilution with the 12% PEG buffer, yielding 200 mL of virus sample in 6% PEG. The majority of contaminants passed through the monolith and the remainder were washed away with equilibration buffer. The column was then eluted with a 10 mL linear gradient to 50 mM Hepes, 600 mM NaCl, pH 7.0. Analytical anion exchange chromatography demonstrated 90% recovery of 90% pure virus, in conjunction with 90% removal of DNA. Subsequent analysis showed that the virus remained infective. A second purification step on an anion exchange monolith achieved greater than 99% purity, with a compound recovery of 80%, and an additional 1000-fold DNA reduction. The entire 2-step process was completed within 2 hours.

Example 22

Preferential exclusion chromatography purification of exosomes. A 1 mL hydroxyl monolith was equilibrated with 6% PEG 6000, 50 mM Hepes, 200 mM NaCl pH 7.0 at 8 mL/min. A preparation of exosomes secreted by mesenchymal stem cells was loaded onto the monolith by in-line dilution with 8% PEG 6000, 50 mM HEPES, 200 mM NaCl pH 7.0 to give an equivalent PEG 6000 concentration of 6%. The monolith was next washed with 6% PEG 6000 and eluted with an 8 mL linear gradient to 50 mM HEPES, 200 mM NaCl pH 7.0. Presence of exosomes was detected on-line by observing absorbance at 600 nm. Dynamic light scattering was used for offline detection. Both detection methods showed the presence of exosomes in the eluate, highlighting the utility of the method to purify organelles.

Example 23

Purification of monoclonal IgG on hydroxyl porous microparticles. 10 mL of Toyopearl HW75M particles were dispersed in 100 mL of an IgG-containing cell culture supernatant. Saturated ammonium sulfate was added over the course of 1 hour to a final concentration of 1.5 M. The particles were placed on a filter and the liquid suctioned off. The particles were then packed in a column, washed with 12.5% PEG-6000 50 mM Hepes, 300 mM NaCl, pH 7.0, then eluted with a 10 column volume descending PEG gradient. It was observed that aggregates eluted later than non-aggregated antibody. Analytical size exclusion chromatography (SEC) showed IgG to be greater than 95% pure.

Example 24

Purification of monoclonal IgG on nonporous silica particles. 5 mL of nonporous silica 10 micron microspheres were dispersed in 100 mL of an IgG-containing cell culture supernatant. Saturated ammonium sulfate was added over the course of 30 minutes to a final concentration of 1.5 M. The particles were placed on a filter and the liquid suctioned off. The particles, still in the filtration apparatus, were washed with 1.5 M ammonium sulfate, which was then suctioned off. The filtrate receptacle was changed, the IgG was dissociated from the particles by addition of 2 bed volumes of 50 mM Hepes, 0.3 M sodium chloride, pH 7.0, then suctioned through the filter. Analytical SEC showed the antibody to be greater than 95% pure.

Example 25

Two-step purification of monoclonal IgG on non-porous silica microspheres. 5 mL of nonporous silica 10 micron microspheres were dispersed in 100 mL of an IgG-containing cell culture supernatant. 30% PEG-6000 in 50 mM Hepes, pH 7.0 was added over the course of 30 minutes to a final concentration of 15%. The particles were placed on a filter and the liquid suctioned off. The particles, still in the filtration apparatus, were washed with 15% PEG, 300 mM sodium chloride, 50 mM Hepes, pH 7.0, which was then suctioned off. The filtrate receptacle was changed, the IgG was dissociated from the particles by addition of 2 bed volumes of 50 mM Hepes, 0.3 M sodium chloride, pH 7.0, then suctioned through the filter. Analytical SEC showed the antibody to be greater than 95% pure. This material was fractionated on a column of hydroxyapatite (CHT type I, 40 micron) to remove IgG fragments and aggregates. Analytical SEC showed the material to be aggregate free, with purity of about 99%.

Example 26

Purification of IgM monoclonal antibody on hydroxyl porous microparticles. 5 mL of Sephadex G25 superfine were dispersed in 100 mL of an IgM containing cell culture supernatant. Saturated ammonium sulfate was added over the course of 15 minutes to a final concentration of 1.2 M. The suspension was applied to a 0.22 micron filter membrane and the liquid suctioned off. The particles were resuspended in 1.2 M ammonium sulfate, and the liquid suctioned off again. The particles were resuspended in 12.5% PEG-6000, 100 mM sodium chloride, 50 mM Hepes, pH 7.0. The filtrate receptacle was changed, the particles resuspended with 50 mM Hepes, 100 mM sodium chloride, pH 7.0, and the antibody-containing liquid suctioned through the filter. Analytical SEC showed the material to be greater than 95% pure.

Example 27

3-step purification of monoclonal IgM. 10 mL of non-porous 10 micron silica microspheres were dispersed in 100 mL of an IgM-containing cell culture supernatant. 30% PEG-6000, 50 mM Hepes, pH 7.0 was added over the course of 30 minutes to a final concentration of 10% PEG. The suspension was applied to a 0.22 micron filter membrane and the liquid suctioned off. The particles were resuspended in 10% PEG-6000, 1 M NaCl, 50 mM Hepes, pH 7.0, and the liquid suctioned off. The filtrate receptacle was changed, the IgM dissociated from the particles by addition of 25 mL 50 mM Hepes, 1 M NaCl, 0.1% polysorbate-20, and the IgM suctioned through the filter. The IgM was then applied to a column of hydroxyapatite (CHT type II, 40 micron and eluted with a Phosphate gradient. The IgM fraction was free of aggregates and fragments. The hydroxyapatite eluate was diluted 1:1 with water and applied to an anion exchange monolith (QA, 8 mL) equilibrated with 50 mM hepes, pH 7.0, then eluted with a linear gradient to 300 mM sodium chloride, 50 mM Hepes, pH 7.0. The IgM was greater than 99% pure and free of aggregates.

Example 28

Purification of antihemophiliac factor (Factor VIII-vWF complex). 1 mL of 10 µm non-porous silica microspheres were dispersed in a 10 mL solution of human recombinant antihemophiliac factor at a concentration of 1 mg/mL and human serum albumin (HSA) at 10 mg/mL. 30% PEG-6000 was in 50 mM Hepes, 100 mM NaCl, pH 7.0 was added to a final concentration of 10%. The suspension was applied, to a 0.22 µm filter and the liquid suctioned off. The particles were resuspended in 10 mL 50 mM Hepes, 100 mM NaCL, 10% PEG-6000, pH 7.0, and the liquid removed. The filter receptacle was changed and the antihemophiliac factor eluted from the particles by resuspending them in 50 mM Hepes, 100 mM NaCl, pH 7.0. HSA was absent from the antihemophiliac factor, of which 67% was recovered.

Example 29

Virus purification. 1 mL of 10 µm non-porous silica microspheres were dispersed in 20 mL of bacteriophage M13.12% PEG-6000 in 50 mM Hepes, 600 mM NaCl, pH 7.0 was added to a final PEG concentration of 6%. The suspension was applied to a 0.22 µm filter and the liquid suctioned off. The particles were resuspended in 10 mL 50 mM Hepes, 600 mM NaCl, 6% PEG-6000, pH 7.0, and the liquid removed. The filter receptacle was changed and the virus eluted from the particles by resuspending them in 50 mM Hepes, 50 mM NaCl, pH 7.0. Analytical anion exchange chromatography demonstrated 30% recovery of 80% pure virus, in conjunction with 90% removal of DNA. Subsequent analysis showed that the virus remained infective.

Example 30

Purification of exosomes. 10 mL of 10 µm non-porous silica microspheres were dispersed in 100 mL of a preparation of exosomes secreted by human stem cells. 30% PEG-6000 in 50 mM Hepes, 200 mM NaCl, pH 7.0 was added to a final PEG concentration of 6%. The suspension was applied to a 0.22 µm filter and the liquid suctioned off. The particles were resuspended in 10 mL 50 mM Hepes, 200 mM NaCl, 6% PEG-6000, pH 7.0, and the liquid removed. The filter receptacle was changed and the exosomes eluted from the particles by resuspending them in 50 mM Hepes, 50 mM NaCl, pH 7.0. Differential light scattering and multiple wavelength monitoring confirmed the presence of exosomes in the eluate.

Example 31

Purification of an IgG using non-porous starch-coated magnetic nanoparticles. To 1 mL samples of Her2 cell culture supernatant, 5 mg of either 200 nm or 1 micron magnetic nanoparticles was added. 45% (w/v) PEG 6000 in 50 mM HEPES 100 mM NaCl pH 7.0 was added to the microcentrifuge tube to a final concentration of 15% PEG 6000 and mixed by hand. The suspension was clarified by application of a magnetic field and the supernatant was removed using a micropipette. Bound IgG was eluted from the particles by suspending the beads in 50 mM HEPES, 100 mM NaCl pH 7.0. Analytical SEC showed IgG to be greater than 95% pure.

Example 32

Figure 6:
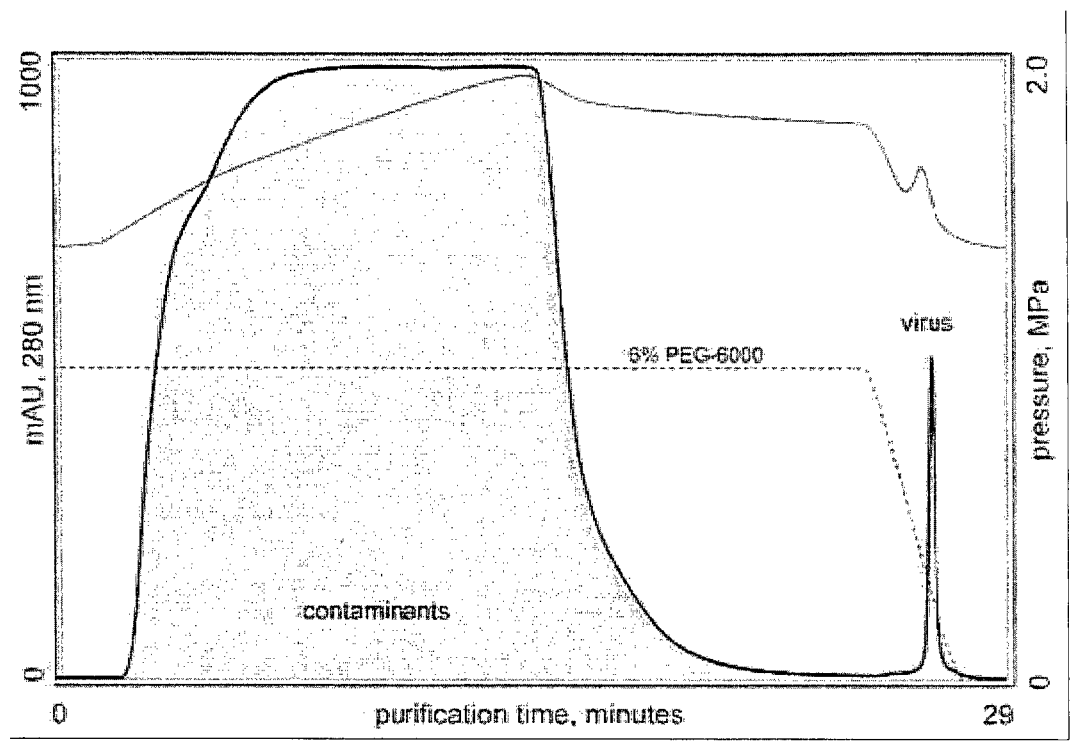
FIG. 6 shows the performance of constrained co-hydration convective chromatography of a monoclonal IgM as described in Example 32 including the influence of the preferentially agent PEG-6000 upon the timing of the elution of contaminants and the target IgM.

Monolith-based CCC purification of virus. Polymethacrylate monoliths with a hydroxylated (OH) surface and average 2 µm channels were used to evaluate the ability of constrained co-hydration to achieve selective retention of virus. Mass transfer in monoliths occurs by convection, which is unaffected by the diffusivity limitations that encumber columns packed with porous particles [Hahn, R., Panzer, M., Hansen, E., Mollerup, J., Jungbauer, A., Monoliths for separation of biomolecules. *Sep. Sci. Technol.*, 37 1545-1565 (2002); Strancar, A., Podgornik, A., Barut, M., Necina, R., Short monolithic columns as stationary phases for biochromatography. *Adv. Biochem. Eng. Biotechnol.* 76 49-85 (2002); Jungbauer, A., Chromatographic Media for Bioseparation, J. Chromatogr. A, 1065 3-12 (2005)]. By extension, chromatography performance is unaffected by viscosity. Monoliths also lack the void space where turbulent shear forces are mainly generated in particle columns [Levy, M. S., O'Kennedy, R. D., Ayazi-Shamlou, P., Dunnill, P., Biochemical engineering approaches to the challenges of producing pure plasmid DNA. *Trends Biotechnol.*, 18 296-305 (2000); Lendero-Krajnc, N., Smrekar, F., Strancar, A., Podgornik, A., Adsorption behavior of large plasmids on the anion-exchange methacrylate monolithic columns. *J. Chromatogr. A.*, 1218 2413-2424 (2011)], and their large channels reduce pressure drop across the bed. Bacteriophage M13 occurs as a weakly flexible rod with a length of 916 nm, a diameter of 7.2 nm, and a molecular weight of about 16.7 MDa24. Filtered *E. coli* supernatant was loaded through one pump and diluted in-line with 12% PEG-6000 delivered through another pump at the same flow rate. Pre-monolith residence time of the virus in the 6% PEG mix was calculated to be about 1 second, insufficient for significant precipitation to occur prior to virus contact with the monolith surface. Transit time through the monolith for unretained substances was about 5 seconds. More than 90% of the virus from a 2.5 L sample was retained by a 0.34 mL monolith, highlighting the rapid binding kinetics and high concentration factor. The monolith was subsequently washed with 6% PEG, 600 mM NaCl, 50 mM Hepes, pH 7.0, then eluted with a linear gradient to 50 mM Hepes, 600 mM NaCl, pH 7.0. The elution profile is reminiscent of affinity chromatography, with nearly all contaminants flowing through the column and the virus recovered in a 2.5 mL fraction (FIG. 6). Dynamic binding capacity determined with purified phage was 9.9×10^12 cfu/mL of monolith. Host cell ELISA documented 99.8% reduction of *E. coli* proteins. AccuBlue documented 92% reduction of DNA. Infectivity of CCC-purified virus was equivalent to unpurified virus, highlighting the benign influence of the separation method and conditions. (See FIG. 6).

Example 33

Figure 7:
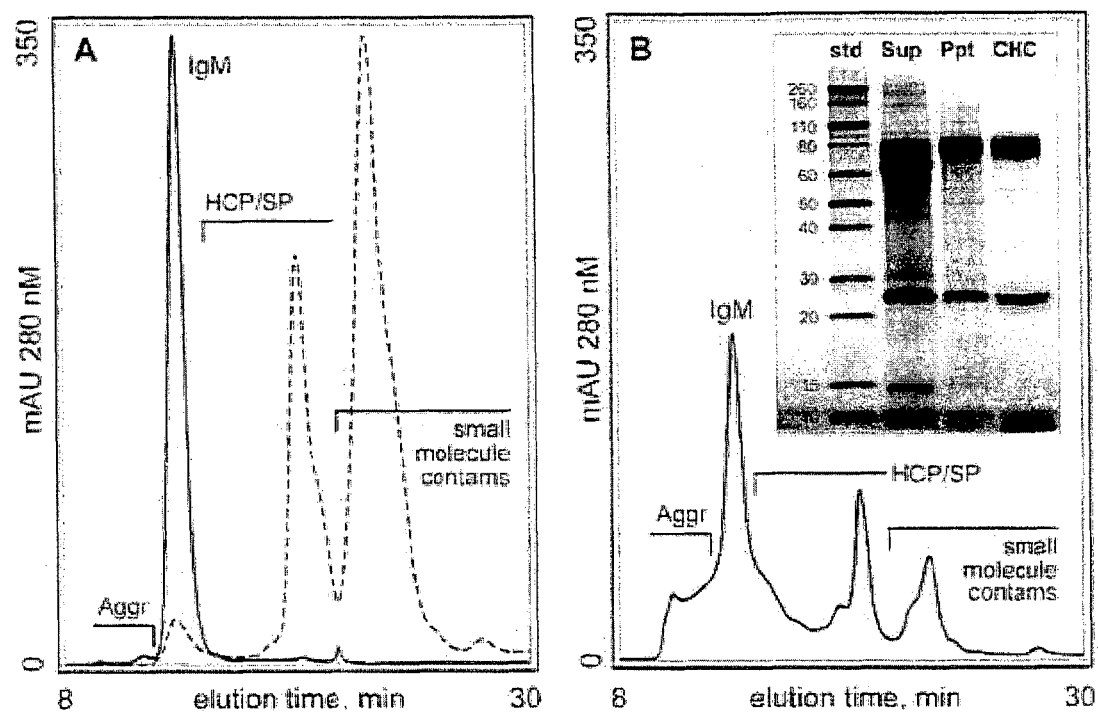
FIGS. 7A and 7B show the performance of constrained co-hydration convective chromatography of a monoclonal IgM as described in Example 33.

Monolith-based CCC purification of IgM. OH monoliths were also used to evaluate the ability of constrained cohydration to achieve selective retention of IgM. This class of antibodies is notoriously labile, with a molecular weight of about 1 MDa25. Monoclonal IgM grown in 20% serum-supplemented cell culture media was loaded by in-line dilution at 1 part supernatant to 4 parts 12.5% PEG-6000, yielding a final PEG concentration of 10%. The monolith was washed with 10% PEG, 200 mM NaCl, 50 mM MES, pH 6.0, then eluted with a linear gradient to 50 mM MES, 200 mM NaCl, pH 6.0. CCC was able to achieve 90% purity and 70% recovery of monoclonal IgM, despite the initial antibody concentration being only about 20 µg/mL (FIG. 7). We have since achieved similar CCC results with more than 20 IgM clones grown under the same conditions. Purity increases up to 95% and recovery up to 90% with higher-producing clones grown in protein-free cell culture media. Dynamic binding capacities for different clones range from 20 to 38 mg IgM/mL monolith. Practical capacity is sometimes determined more by pressure than surface availability, since pressure increases linearly throughout the sample loading process. This is believed to result from gradual narrowing of the monolith's channels by accretion of protein on their surfaces or, as shown in FIG. 6, mediated by virus. (See FIG. 7).

The present invention may be combined with other purification methods to achieve higher levels of purification. Examples include, but are not limited to, other methods commonly used for purification of proteins or virus, such as other precipitation methods, affinity chromatography, anion exchange chromatography, cation exchange chromatography, hydrophobic interaction chromatography, immobilized metal affinity chromatography, and additional mixed mode chromatography methods. It is within the purview of a person of ordinary skill in the art to develop appropriate conditions for the various methods and integrate them with the invention herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, operating conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method for purification of a hydrated target species of biological origin in a sample comprising the steps of contacting the sample with a hydrated surface of an undissolved material and contacting the sample with a constraining agent in an amount sufficient to cause more than 50% to substantially all of the target species to be retained at the hydrated surface of the undissolved material, wherein
  (i) the undissolved material comprises particles,
  (ii) a surface of the particles includes charged moieties,
  (iii) the target species is retained exclusively by constrained cohydration under conditions providing a substantial absence of a direct chemical interaction between the target species and the hydrated surface, and
  (iv) the conditions that provide the substantial absence of a direct chemical interaction comprise pH, conductivity and salt concentration of buffers delivered to a column of the particles, wherein said conditions discourage direct interaction between the hydrated target species and the charged moieties, and wherein the particles are optionally a convective chromatography material.

2. The method of claim 1, wherein the hydrated target species is a virus.

3. The method of claim 1, wherein the sample is a virus-containing solution derived from cell culture.

4. The method of claim 1, wherein the surface of the undissolved material has one or more polar chemical moieties comprising a hydroxyl group.

5. The method of claim 1, wherein the constraining agent comprises a non-ionic organic polymer.

6. The method of claim 5, wherein the non-ionic organic polymer comprises polyethylene glycol.

7. The method of claim 6, wherein the polyethylene glycol has an average polymer weight between 100 and 10,000 D or between 600 and 8,000 D.

8. The method of claim 6, wherein the polyethylene glycol is provided at a concentration between approximately 2% and 50% (w/v).

9. The method of claim 6, wherein the polyethylene glycol is provided at a concentration between approximately 2% and 25% (w/v) with the polyethylene glycol having an average polymer weight above about 6,000 D.

10. The method of claim 6, wherein the polyethylene glycol is provided at a concentration between approximately 15% and 50% (w/v) with the polyethylene glycol having an average polymer weight below about 6,000 D.

11. The method of claim 6, wherein the polyethylene glycol is provided at a concentration between approximately 2% and 25% (w/v) with the polyethylene glycol having an average polymer weight between about 4,000 D and about 8000 D.

12. The method of claim 1, wherein the particles comprise microparticles.

13. The method of claim 1, wherein the particles comprise magnetic particles.

14. The method of claim 1, wherein the particles comprise metal-core particles having a polymer coating.

15. The method of claim 1, wherein the particle size is (a) between about 100 nm and about 500 µm, or (b) between about 100 nm and about 50 µm, or (c) between about 100 nm and about 4 µm, or (d) between about 100 nm and about 3 µm, or (e) between about 100 nm and about 1 µm, or (f) between about 200 nm and about 2 µm, or (g) between about 200 nm and about 500 nm, or (h) 500 nm and about 1 µm, or (i) between about 5 µm and about 50 µm.

16. The method of 1, wherein the step of contacting the target sample with the particles occurs prior to the step of contacting the sample with the constraining agent.

17. The method of claim 1, comprising the additional steps of separating the particles with the target species associated with the hydrated surface of the particles from the liquid phase and dissociating the target species from the particles.

18. The method of claim 17, wherein the step of dissociating the target species consists of washing the particles with a solution where the solution contains the constraining agent in an amount insufficient to retain the target species at the hydrated surface of the particles.

19. The method of claim 17, wherein an agent which effects dissociation of the target species from the hydrated surface of the particles comprises a surfactant.

20. The method of claim 1, wherein the constraining agent is added to the sample and the particles over a period of time from about one minute to about five hours; between 2 min and 15 min; between 2 min and 30 min; between 10 min and 30 min; between 2 min and 2 hours; or between about 2 min and 1 hour.

21. The method of claim 1, wherein the particles are separated from the liquid component of the mixture by filtration.

22. The method of claim 21, wherein the separated particles are washed with a solution comprising the constraining agent.

23. The method of claim 17, wherein the step of dissociating is carried out in a single step of adding a dissociating buffer to the particles.

24. The method of claim 1, wherein the method is performed prior to or after a method for fractionating the target species from other materials is performed and the method for fractionating comprises anion exchange chromatography.

25. The method of claim 1, wherein the particles are a convective chromatography material and the convective chromatography material comprises a monolith.

26. The method of claim 25, wherein the monolith is comprised of polymethacrylate.

27. The method of claims 25, wherein the monolith has an average channel size between about 1 micron and 200 micron.

28. The method of claim 27, wherein the channel size is between about 1 micron and 5 microns or between about 10 micron and 20 microns, or between about 50 micron and 200 microns.

29. The method of claim 25, wherein the monolith is chemically modified to increase its capacity for the hydration of its surface.

30. The method of claim 1, wherein the particles are a convective chromatography material and the convective chromatography material is hydroxylated.

31. The method of claim 30, wherein (i) the convective chromatography material includes charged moieties and (ii) wherein said conditions suspend direct interaction between the target species and such charged moieties during at least a portion of the step of contacting the sample with the constraining agent so that during that portion the target species is retained at the hydrated surface exclusively by constrained cohydration.

32. The method of claim 1, wherein the particles are the convective chromatography material and the step of contacting the sample with the constraining agent is performed by in-line dilution prior to contacting the sample with the convective chromatography.

33. The method of claim 32, wherein the convective chromatography material is equilibrated with the constraining agent prior to contacting of the sample with the convective chromatography material.

34. The method of claim 32, comprising the additional steps of washing the hydrated convective chromatography material with a solution comprising the constraining agent in an amount sufficient to remove contaminants not retained at the hydrated surface of the undissolved material, and subsequently dissociating the target species from the convective chromatography material.

35. The method of claim 34, wherein the step of dissociating the target species comprises washing the convective chromatography material with a solution where the solution contains the constraining agent in an amount insufficient to retain the target species at the hydrated surface of the convective chromatography material.

36. The method of claim 1, wherein the method is performed prior to or after a method for fractionating the target species from other materials is performed, and the method for fractionating comprises anion exchange chromatography.

\* \* \* \* \*